United States Patent
Thompson et al.

(10) Patent No.: US 10,504,380 B2
(45) Date of Patent: Dec. 10, 2019

(54) MANAGING PRESENTATION OF FITNESS ACHIEVEMENTS

(71) Applicant: Apple Inc., Cupertino, CA (US)

(72) Inventors: Aaron P. Thompson, San Francisco, CA (US); Anders K. Haglunds, Mountain View, CA (US); Jay C. Blahnik, San Francisco, CA (US)

(73) Assignee: Apple Inc., Cupertino, CA (US)

(*) Notice: Subject to any disclaimer, the term of this patent is extended or adjusted under 35 U.S.C. 154(b) by 366 days.

(21) Appl. No.: 15/272,203

(22) Filed: Sep. 21, 2016

(65) Prior Publication Data
US 2017/0358242 A1    Dec. 14, 2017

Related U.S. Application Data

(60) Provisional application No. 62/348,536, filed on Jun. 10, 2016.

(51) Int. Cl.
*G09B 19/00*      (2006.01)
*A63B 24/00*      (2006.01)
(Continued)

(52) U.S. Cl.
CPC ........ *G09B 19/003* (2013.01); *A63B 24/0062* (2013.01); *G06F 9/542* (2013.01); *G06Q 10/0639* (2013.01); *G06Q 50/22* (2013.01); *G09B 5/125* (2013.01); *G16H 20/30* (2018.01); *G16H 40/63* (2018.01); *G16H 40/67* (2018.01)

(58) Field of Classification Search
CPC . G06F 19/3481; G06F 3/048; A63B 24/0062; A63B 2225/50; A63B 71/0622; G09B 19/00; G09B 19/003; G09B 19/0092; G09B 19/0038; A61B 5/1118; A61B 5/0022; A61B 5/486; G16H 20/30; G16H 10/60; G16H 20/60
See application file for complete search history.

(56) References Cited

U.S. PATENT DOCUMENTS

| 2013/0218585 | A1 | 8/2013 | Watterson |
| 2016/0058336 | A1 | 3/2016 | Blahnik et al. |

FOREIGN PATENT DOCUMENTS

| EP | 2434440 A1 | 3/2012 |
| WO | 2012021507 A2 | 2/2012 |

OTHER PUBLICATIONS

International Preliminary Report on Patentability dated Dec. 20, 2018 in International Application No. PCT/US2017/031246. 13 pages.
(Continued)

*Primary Examiner* — Jerry-Daryl Fletcher
(74) *Attorney, Agent, or Firm* — Kilpatrick Townsend & Stockton

(57) ABSTRACT

A fitness achievement definition may define a fitness achievement using trigger information and one or more achievement rules. The fitness achievement may be earnable by a user of a user device by meeting the requirements of the fitness achievement. The fitness achievement definition may be stored on a user device that includes an application that collects data including fitness data. Detection of a trigger event corresponding to the trigger information and evaluation of the achievement rules may be managed by the user device. In some examples, a fitness communication relating to the fitness achievement may be presented at the user device.

19 Claims, 11 Drawing Sheets

(51) Int. Cl.
  *G09B 5/12*    (2006.01)
  *G06F 9/54*    (2006.01)
  *G16H 40/63*   (2018.01)
  *G16H 40/67*   (2018.01)
  *G16H 20/30*   (2018.01)
  *G06Q 10/06*   (2012.01)
  *G06Q 50/22*   (2018.01)

(56) References Cited

OTHER PUBLICATIONS

PCT/US2017/031246 "International Search Report and Written", dated Jul. 13, 2017, 514 pages.

MANAGING PRESENTATION OF FITNESS ACHIEVEMENTS

CROSS-REFERENCE TO RELATED APPLICATION

This application claims the benefit of U.S. Provisional Application No. 62/348,536, filed Jun. 10, 2016 entitled "Managing Presentation of Fitness Achievements." The disclosure of this application is incorporated by reference herein in its entirety.

BACKGROUND

Major updates to software running on electronic devices such as mobile phones, tablets, wearable devices, and the like are typically downloaded and installed in response to a user selecting a prompt relating to the updates. For example, the user may receive a notification that a new software update is available for her electronic device. The user may then select a time that is convenient for downloading and installing the update. Depending on the size of the update and the network speed, downloading may take a few seconds, a few minutes, or substantially more time. Additionally, depending on the scope of the update and other details (e.g., presence of executable code, etc.), certain conditions may be required in order for the update to be installed (e.g., the electronic device being plugged into a charging outlet, the electronic device being rebooted after installation, input of user credentials, etc.). The combination of time required for updates and these conditions may present challenges to the user and may even result in the update not being selected in a timely manner. This can result in a poor user experience when out-of-date software continues to be used. Because of this, software developers may attempt to minimize the number of major updates. One way of doing this is to send certain minor updates to electronic devices "over-the-air." These minor updates may be downloaded in the background and installed without user interaction. However, for security reasons or otherwise, the type of updates that may be sent to the electronic devices in this manner may be limited.

Generally, in recent years, computing capacity of electronic devices has increased. At the same time, these electronic devices are required to support more and more functionality. For example, mobile phones are able to support different applications, some of which may run multiple processes in parallel. Even with such increased computing capacity, prioritization of computing resources may impact user experience and overall operational integrity of the electronic devices. This may be especially true of electronic devices that include functions performed in response to detection of certain conditions. Continually evaluating such conditions, however, may be an inefficient use of computing resources, not to mention may result in increased power consumption.

BRIEF SUMMARY

Embodiments of the present disclosure can provide systems, methods, and computer-readable medium for managing fitness achievements. According to one embodiment, a method may be implemented by a computer system to at least receive, by a fitness application of a wearable device, a non-executable fitness achievement definition that defines a fitness achievement. The non-executable fitness achievement definition may include trigger information, one or more conditional statements having at least one criteria corresponding to the fitness achievement, and image data corresponding to a fitness achievement graphical element. The method may also include storing the non-executable fitness achievement definition on the wearable device. The method may also include accessing, by the fitness application, data tracked by the fitness application and collected by the wearable device, at least a portion of the data may include fitness data. The method may also include detecting a trigger event based at least in part on a comparison of the trigger information to the data tracked by the fitness application. The method may also include evaluating, at least in response to detecting the trigger event, the one or more conditional statements against the at least one criteria using one or more of the data or other data tracked by the fitness application to generate an output. The method may also include presenting, based at least in part on the output, a fitness communication on the wearable device. The fitness communication may correspond to the fitness achievement.

According to one embodiment, a method may be implemented by a computer system to at least receive, by a fitness application of a user device, a fitness achievement definition that defines a fitness achievement. The fitness achievement definition may include trigger information and one or more conditional statements having at least one fitness achievement criteria. The method may also include storing the fitness achievement definition on the user device. The method may also include managing a plurality of conditional statements previously stored on the user device. The method may also include comparing the trigger information to data tracked by the fitness application to detect a trigger event. The method may also include selecting, in response to detecting the trigger event, a conditional statement from a set of conditional statements including the one or more conditional statements and the plurality of conditional statements. The method may also include presenting, based at least in part on selecting the conditional statement, a fitness communication corresponding to the fitness achievement.

According to one embodiment, one or more computer-readable medium storing computer-executable instructions is described. The computer-executable instructions, when executed by a processor, configure a processor to perform operations including managing a plurality of achievement rules stored on a user device. The operations may also include receiving data tracked by a fitness application. The operations may also include comparing the data to trigger information of a fitness achievement definition to identify a trigger event. The achievement definition may include the trigger information and an achievement rule corresponding to the trigger information. The operations may also include selecting, based at least in part on the fitness achievement definition, at least one achievement rule from a set of achievement rules including the plurality of achievement rules and the achievement rule. The operations may also include determining that the at least one achievement rule is fulfilled. The operations may also include presenting, at least in response to determining that the at least one achievement rule is fulfilled, a fitness communication corresponding to the fitness achievement.

DETAILED DESCRIPTION

Figure 1:
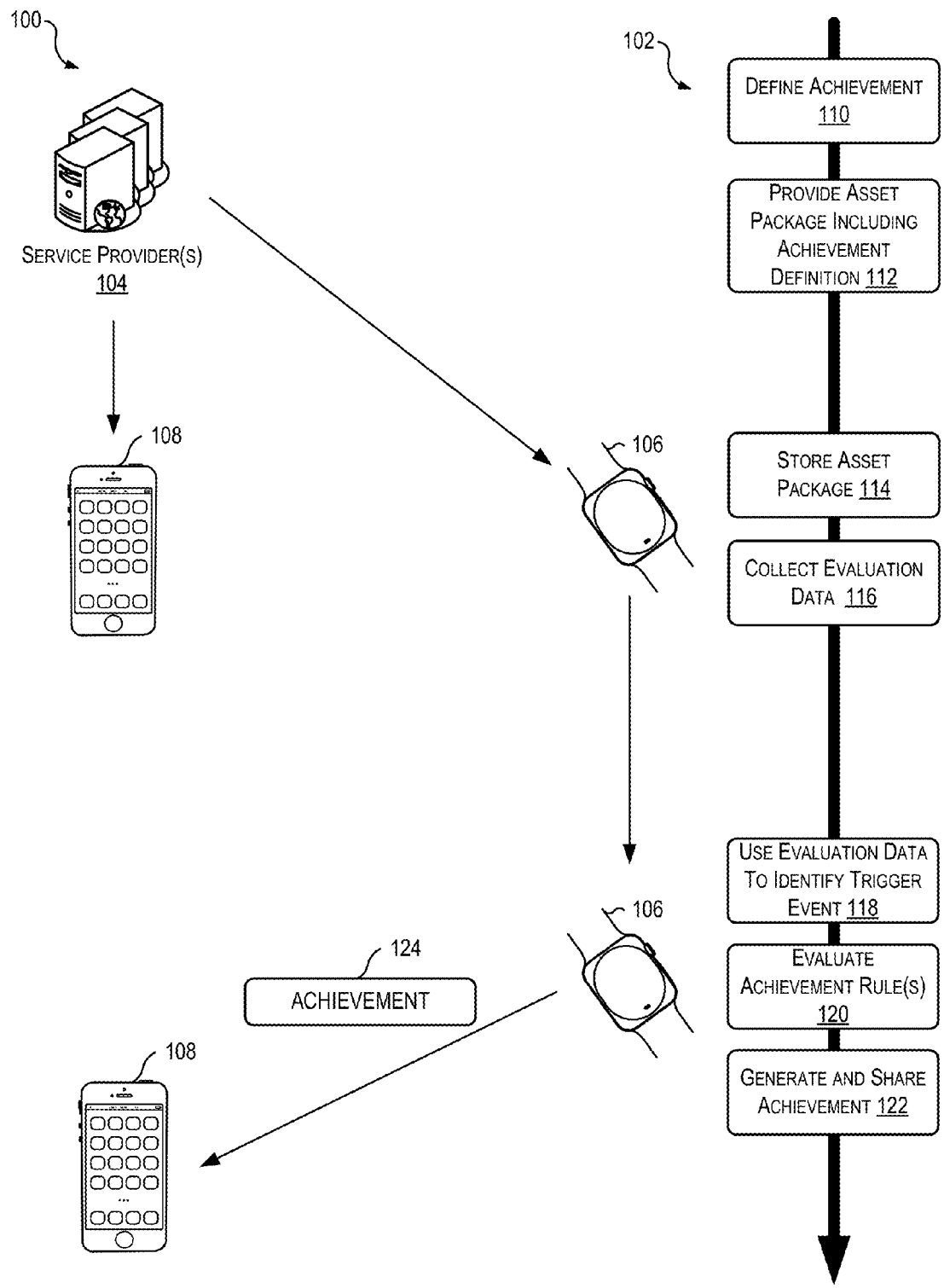
FIG. 1 illustrates a simplified block diagram depicting an example flow for managing presentation of achievements as described herein, according to at least one example.

In the following description, various examples will be described. For purposes of explanation, specific configurations and details are set forth in order to provide a thorough understanding of the examples. However, it will also be apparent to one skilled in the art that the examples may be practiced without the specific details. Furthermore, well-known features may be omitted or simplified in order not to obscure the example being described.

Examples of the present disclosure are directed to, among other things, methods, systems, and computer-readable media for managing presentation of achievements using user devices. Generally, achievements may be electronic awards given to users who accomplish certain fitness-related goals. In some examples, certain achievements can be associated with a fitness challenge such that completion of the fitness challenge will result in a user receiving one or more corresponding achievements. In other examples, achievements can be earned by the user as part of the user conducting her normal fitness routine.

An achievement can include, among other things, any suitable media content (e.g., video, image, audio, text, etc.) that describe the achievement and can be displayed on a user device. The techniques described herein ensure that the achievement is awarded to the user at or shortly after the user achieves the fitness-related goal corresponding to the achievement. In this manner, the user can receive the immediate gratification that comes from achieving goals. To ensure timely presentation of the achievement, a user device such as a wearable device or other electronic device can be used to evaluate whether achievements should be awarded. Achievements can be defined using an achievement definition. The achievement definition can be evaluated in a manner that provides for presentation of achievement awards in a timely (e.g., proximity in time to a user reaching a fitness goal) and computationally efficient manner (e.g., conserves computational resources and power resources of corresponding user devices). Moreover, because certain achievements may be time sensitive (e.g., available for a limited duration), the techniques described herein provide for delivery of achievement definitions for evaluation on user devices at times outside of a typical software update cycle. The achievement may be defined in a manner that does not include executable code. Thus, sending the achievement definitions to the user devices over the air (e.g., outside of a typical software update cycle) may present less of a security risk than if the achievements relied on executable code.

Fitness data of a user that indicates any suitable aspect of the user's physical activities (e.g., calories burned, workouts, standing, walking, running, etc.) can be tracked by a fitness application of a wearable device. The fitness application may also have access to other system data such as date, time, holiday calendar, geographic location, user profile data, and the like. The fitness data and the system data (collectively "evaluation data") can be used by the wearable device, or other suitable device, as part of evaluating whether the user has earned an achievement. Because the evaluation data is sometimes used for other purposes by the fitness application, the techniques described herein can utilize one or more existing events (e.g., fitness-related events) generated based at least in part on the evaluation data to determine when to evaluate whether an achievement has been earned by the user. For example, a certain achievement may require the user to accomplish a certain workout. After the user completes the workout, the fitness application can automatically generate and save a workout event that indicates that the workout was completed and saved. The saved workout event can be used as a trigger to call up one or more achievement rules. The one or more achievement rules can be evaluated to determine whether the achievement should be awarded to the user. If so, an achievement award (e.g., a user interface element) can be generated and provided to the user (e.g., using a notification presented on a display of the wearable device). A graphical representation of the achievement award can be displayed in a digital (e.g., virtual) trophy case within an application running on the wearable device or other electronic device (e.g., a mobile phone associated with the wearable device). If not, no achievement award may be generated and no notification may be sent to the user.

FIG. 1 illustrates a simplified block diagram 100 depicting an example process 102 for managing presentation of achievements, according to at least one example. The diagram 100 can include one or more service provider computers 104 (the "service provider 104"), a wearable device 106, and an electronic device 108. The wearable device 106 may be associated with the electronic device 108 (e.g., a host device). In some examples, this may include the wearable device 106 being paired with the electronic device 108 in any suitable manner. Pairing of the two devices 106 and 108 may enable the electronic device 108 to function as a proxy for the wearable device 106. The wearable device 106, the electronic device 108, the service provider 104, or any suitable combination of the wearable device 106, the electronic device 108, and the service provider 104 may implement aspects of the techniques described herein.

The process 102 may begin at 110 by the service provider 104 defining an achievement 124. For example, the service provider 104 may provide an achievement editor interface for use by an achievement editor to define a new achievement (e.g., the achievement 124). The achievement editor may utilize any suitable user device (e.g., a desktop computer, a laptop computer, a tablet device, the electronic device 108, the wearable device 106, and the like) to access the achievement editor interface. The achievement editor may be a user associated with the service provider 104 and/or a third-party user who has been given access to the achievement editor interface. Using the achievement editor interface, the achievement editor can define new achievements, edit existing achievements, request testing of achievements under actual or simulated conditions, and/or send achievement definitions to a set of user devices (e.g., the electronic device 108, the wearable device 106, and/or sets of such devices). As described herein, the user devices can use the achievement definitions to determine whether their respective users have earned the corresponding achievements.

In some examples, the achievement 124 can be defined by an achievement definition. The achievement definition may represent a data file that is non-executable. Instead, as described herein, the data file can include aspects that can be parsed by the wearable device 106 and/or the electronic device 108. To this end, the achievement definition can include an achievement identifier, trigger information, one or more achievement rules, an achievement image, and/or any other suitable information. The achievement identifier can uniquely identify the achievement 124 from among other achievements. The trigger information can indicate what fitness events occurring at the wearable device 106 and/or the electronic device 108 will trigger evaluation of the one or more achievement rules. The achievement rules can indicate one or more conditions, the fulfillment of which will result in generation of the achievement. The achievement image can represent the achievement 124 and function as a reminder to the user that she was awarded the achievement. The achievement image can be stored together with other achievement images for other earned achievements and displayed together in an achievement dashboard. The achievement dashboard can be provided by a fitness application of the electronic device 108 and/or the wearable device 106. In some examples, the achievement definition can include other data such as text strings for display when the achievement 124 is earned, other images relating to different states of the achievement image (e.g., unearned visible state, earned visible state, etc.), alert information (e.g., when and what to provide to users about achievements), and any other suitable data relating to the achievement 124.

At 112, the service provider 104 can provide an asset package including the achievement definition to the wearable device 106 and/or the electronic device 108. In some examples, the asset package includes the achievement definition corresponding to the achievement 124 together with other achievement definitions and/or other data unrelated to achievements. In some examples, a first portion of the achievement definition is provided in a first asset package and a second portion of the achievement definition is provided in a second asset package. The first asset package may include the achievement identifier, the trigger information, the one or more achievement rules for the achievement, and other similar information for other achievements. The second asset package may include the achievement image and any other data associated with the achievement not provided in the first asset package.

The asset package (or the first asset package and the second asset package) may be provided to the wearable device 106 and/or the electronic device 108 outside of a major software update cycle relating to software running on the wearable device 106 and the electronic device 108. In some examples, this may enable the achievement editor to send achievements to the wearable device 106 and/or the electronic device 108 in preparation for upcoming events such as holidays, activity oriented events (e.g., races), personal events (e.g., birthdays), local/national/international events, and the like.

At 114, the wearable device 106 and/or the electronic device 108 can store the asset package (or the first asset package and the second asset package) received at 112 locally. In this manner, applications of the wearable device 106 and/or the electronic device 108 can access the asset package (or the first asset package and the second asset package) including the achievement definition. Storing the asset package (or the first asset package and the second asset package) can include storing the data in a data file, data structure, data store, memory, or the like.

At 116, the wearable device 106 collects evaluation data (e.g., system data, user data, configuration data, fitness data, etc.). System data can include any suitable data relating to the operation of the wearable device 106 and/or other devices with which the wearable device 106 interacts. The system data can also include data relating to communications between the wearable device 106 and the other devices described herein. In some examples, evaluation data can be collected from one or more other devices and/or applications. For example, a user may utilize a cycling application to track her fitness data relating to cycling. The techniques described herein may use the fitness data from the cycling application for all suitable purposes described herein (e.g., identifying trigger events, evaluating achievement rules, etc.).

As described in detail herein, the wearable device 106 can include any suitable sensors to collect fitness data from a human user. This fitness data can include any suitable data relating to activities performed by the user and/or the health of the user. In some examples, a fitness application of the wearable device 106 may be configured to manage the fitness data collected from the user and other data. Such fitness data may indicate, for the user, a pulse rate, a heart rate, a weight, a heart rate variability measure, temperature data, a number of steps in a period, an amount of time standing and sitting, a number of calories burned, a number of minutes exercised, a history of fitness data, workouts performed, and/or any other suitable data. In some examples, a fitness application running on the wearable device 106 collects the fitness data. The fitness application of the wearable device 106 can store at least a portion of the fitness data and share the fitness data with a fitness application running on the electronic device 108. In some examples, the wearable device 106 and/or the electronic device 108 may share the fitness data (or other evaluation data) with the service provider 104.

At 118, the wearable device 106 and/or the electronic device 108 uses the evaluation data collected by the wearable device 106 to identify a trigger event. The trigger information included in the achievement definition may define the trigger event, and the wearable device 106 and/or the electronic device 108 may monitor and/or collect the evaluation data to detect when the trigger event takes place.

In some examples, detection of trigger events in this manner may conserve computing resources. For example, the trigger events can function as preconditions to evaluating the achievement rules. And because evaluation of the achievement rules may be computationally intensive, the rules may only be evaluated after a trigger event has been registered. This may result in substantial power savings compared to a system that constantly evaluates achievement rules. In addition, because the trigger events are tied to actual evaluation data (e.g., fitness data), which is collected in real time, the techniques described herein may provide a more timely evaluation of the achievement rules when compared to a system that attempts to conserve power by only evaluating periodically (e.g., every 15 minutes).

At 120, the wearable device 106 and/or the electronic device 108 evaluates the achievement rules associated with the trigger event. In some examples, the trigger event may be associated with one or more achievement rules corresponding to a single achievement definition or corresponding to more than one achievement definition. In this manner, detecting the trigger event at 118, may result in evaluation of achievement rules for multiple achievements. The achievement rules may include one or more conditional statements written in any suitable format. For example, the conditional statements may be prepared using the NSPredicate class belonging to one or more of Objective-C, Swift, or Cocoa.

At 122, the wearable device 106 and/or the electronic device 108 generates and shares the achievement 124. For example, when the achievement rules evaluate to true, the process 102 may generate the achievement 124. This can include retrieving the achievement image and corresponding text and presenting the same on the wearable device 106 and/or the electronic device 108. In some examples, generating the achievement 124 can include changing a state of an achievement image in an achievement dashboard from unearned to earned. Information about the generated achievement 124 can be shared between the wearable device 106, the electronic device 108, and the service provider 104. In some examples, notifications and/or messages may be sent to other user devices. For example, information the achievement earned by the user may be sent to user devices associated with friends of the user. In some examples, the achievement 124 is considered a fitness communication. The fitness communication may identify aspects of the conditions that allowed the user to earn the achievement (e.g., trigger events, conditions fulfilled, etc.).

Figure 2:
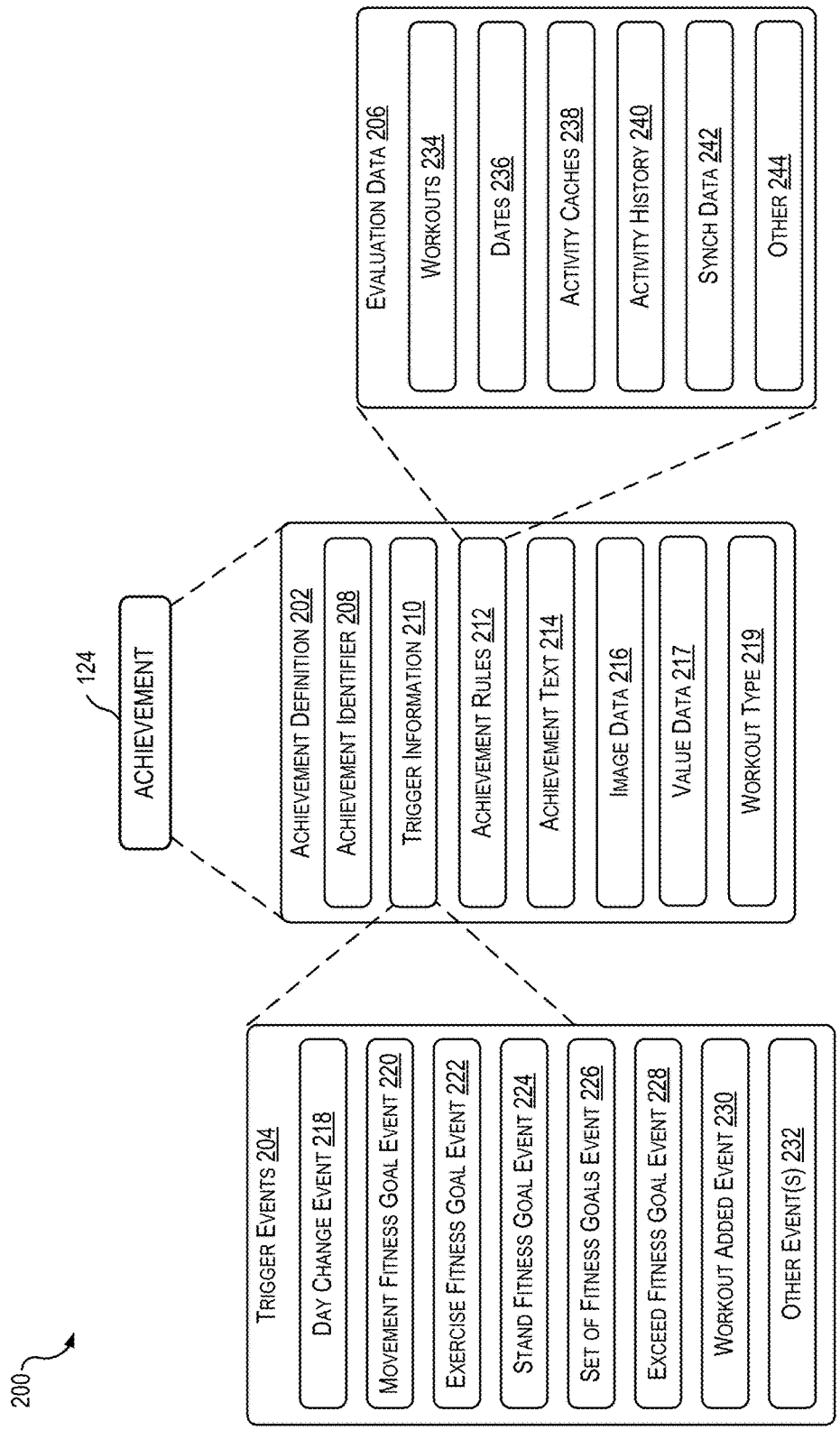
FIG. 2 illustrates a simplified block diagram depicting aspects of an achievement definition for managing presentation of achievements as described herein, according to at least one example.

FIG. 2 illustrates a simplified block diagram 200 depicting aspects of an achievement definition 202 for use in implementing techniques relating to managing presentation of achievements, according to at least one example. The achievement definition 202 can correspond to the achievement 124. The achievement definition 202 can be included in an asset package, sent to a user device (e.g., the wearable device 106 and/or the electronic device 108), and saved by the user device. The block diagram 200 also includes trigger events 204 and evaluation data 206, which can each be referenced by one or more aspects of the achievement definition 202. As introduced herein, the achievement definition 202 can include data such as an achievement identifier 208, trigger information 210, achievement rules 212, achievement text 214, image data 216, value data 217, and workout type 219. It is understood, however, that data of the achievement definition 202 can be stored across multiple devices and can be provided at different times to any one or more of the multiple devices. In addition, the achievement 124 can be defined using less data or more data than described with reference to the achievement definition 202. In some examples, the achievement definition 202 can include the achievement identifier 208, a completed date, the value data 217, and a workout type 219.

The achievement identifier 208 can be used to identify the achievement 124 to which the achievement definition 202 corresponds. The achievement identifier 208, in some examples, may uniquely identify the achievement 124 in a manner that the achievement 124 can be distinguished from all other achievements, or at least other achievements stored on the wearable device 106 and/or the electronic device 108. The achievement identifier 208 may be machine-readable, and, in some examples, may have human-readable aspects as well.

The trigger information 210 can identify one or more trigger events that, when detected, cause an application described herein to evaluate the achievement rules 212. In some examples, the trigger information 210 can identify only a single trigger, which can correspond to one or more of the achievement rules 212. In other examples, the trigger information 210 can identify more than one trigger, each of which can correspond to the same achievement rules 212 and/or different achievement rules 212. In some examples, the trigger events may be considered fitness events that relate to fitness data of a user collected, tracked, processed, and/or stored by the wearable device 106 and/or the electronic device 108. In some examples, the total number of trigger events may be limited. In this manner, different achievements may share the same trigger information 210, but may include different achievement identifiers, achievement rules, achievement text, and/or image data.

The trigger events 204 are examples of trigger events that can be referenced by the trigger information and detected by the wearable device 106 and/or the electronic device 108. The trigger events 204 can include, for example, a day change event 218 (e.g., a change in a system calendar from a first date to a second date), achievement of a movement fitness goal event 220 (e.g., achievement of a goal to move a certain number of steps or burn a certain number of calories over a time period) achievement of an exercise fitness goal event 222 (e.g., achievement of a goal to exercise a certain number of minutes over a time period), achievement of stand fitness goal event 224 (e.g., achievement of a goal to stand a certain number of minutes or according to a certain interval over a time period), achievement of a set of fitness goals event 226 (e.g., achievement of a movement fitness goal, an exercise fitness goal, and a stand fitness goal), achievement of a fitness goal beyond a certain amount event 228 (e.g., achievement of one of the fitness goals by 200% of the fitness goal units), completion of a workout event 230 (e.g., the system saves a workout completed by a user), and any other suitable event 232 generated by the wearable device 106 and/or the electronic device 108 as part of collecting, tracking, processing, and/or storing evaluation data.

The achievement rules 212 can be defined to include one or more conditional statements using one or more evaluation data 206 and one or more criteria. In some examples, the one or more conditional statements can be evaluated to generate an output. The output can include a true or false designation. If true, the achievement 124 will be awarded. If false, the achievement 124 will not be awarded. In some examples, the output can be data other than true or false. For example, the output can indicate—in terms of percentage or the like—how close the user is to fulfilling the requirements for the achievement. The criteria can be numbers, percentages, and the like included in the achievement rules to which the evaluation data 206 can be compared to the conditional statements.

Generally, the evaluation data 206 can include data relating to workouts, goals (e.g., movement goals, stand goals, activity goals, etc.), time spent exercising, historical data such as counters, etc. In some examples, data in the evaluation data 206 can be organized, for example, based at least in part on workouts 234, dates 236, activity caches 238, activity history 240, synch data 242, and any other data 244 that can be included in the achievement rules 212 and/or used when the achievement rules 212 are evaluated. The workouts 234 can include data that identifies types of fitness workouts. These may be workouts that are capable of being captured by and/or entered on the wearable device 106 and/or the electronic device 108 (e.g., running, walking, cycling, kickboxing, swimming, etc.). The workouts 234 can also include data that identifies the actual workouts performed by the user (e.g., swimming) and details surrounding such workouts (e.g., date range, time spent on workout, etc.). In some examples, the workouts 234 are captured, detected, or otherwise saved based at least in part on fitness data and stored in a workout table or other suitable data structure. For example, one or more sensors on the wearable device 106 can receive sensor information while a user is running. The wearable device 106 can use the sensor information to infer that the user is running. When the user finishes running, the wearable device 106 can automatically add a running workout (and associated details) to the workout table.

The dates 236 can include data indicating dates and times at which fitness events or other events were recorded (e.g., first day a user wore the wearable device 106, a current day's date, the date a certain achievement was reached or a certain fitness goal was achieved, etc.). The dates 236 can also include any suitable data relating to availability of the achievement 124 itself (e.g., beginning and end dates of a fitness challenge corresponding to the achievement or beginning and end dates of visibility of an achievement image in an achievement user interface). The dates 236 can be stored in a table or any other suitable data structure.

The activity caches 238 can include fitness data that has been collected by the wearable device 106 and stored by the wearable device 106, the electronic device 108, and the service provider 104. The data can be stored in a manner that indicates whether the data for a given time period resulted in achievement of a fitness goal, receiving of an achievement, or the like. For example, the activity caches 238 can include data collected yesterday and indicating whether or not the user achieved a movement fitness goal. In some examples, the activity caches 238 simply include data that indicates when certain activity goals have been reached. In other examples, the activity caches 238 include data that indicates not only when/whether the activity goals were reached, but also the actual data collected by the wearable device 106 and used to determine whether or not the activity goals were reached. The data associated with the activity caches 238 can be stored in a table or other suitable data structure.

The activity history 240 can include historical fitness data collected by the wearable device 106. The activity history 240 may be maintained on the wearable device 106, the electronic device 108, and/or the service provider 104. In some examples, the activity history 240 indicates historical fitness data relating how the user faired over a time period (e.g., a day, a week, a month, a year, etc.) with respect to one or more activity goals. In some examples, the data associated with the activity history 240 is stored in the form of one or more counters that counter the number of times the user has achieved a goal, etc. The data associated with the activity history 240 can be stored in a table or any other suitable data structure.

The synch data 242 can include locations for storing data relating to synchronizing data across multiple devices. For example, the synch data 242 can include an achievement flag that indicates whether one or both of the wearable device 106 and the electronic device 108 have the appropriate data corresponding to the achievement 124. For example, the wearable device 106 may be configured to detect trigger events, evaluate rules, and generate an achievement. The electronic device 108 may be configured to receive notifications about achievements and store achievement images. For a particular achievement, for example, the synch data 242 can indicate that the wearable device 106 has downloaded the achievement definition, so it can detect trigger events, evaluate rules, and generate the achievement. The synch data 242 can also indicate that the electronic device 108 has downloaded the achievement image, so it can process notifications about the achievement and present the achievement image.

The other data 244 can include any other suitable data relating to the environment in which the wearable device 106 and/or the electronic device 108 operates. For example, the other data 244 can include data describing location information (e.g., country or region, geolocation data, GPS data, etc.) and user profile information (e.g., gender, height, weight, etc.), which may be relevant to a particular achievement rule, and any other suitable information.

Returning now to the achievement text 214, the achievement text 214 can include any suitable strings of text and/or rules for creating text that can be presented together with notifications about the achievement 124, display of the achievement 124, and the like. The achievement text 214 can be particularized to the user of the wearable device 106 and/or the electronic device 108 and particularized to the wearable device 106 and/or the electronic device 108.

The image data 216 can include any suitable images and/or metadata descriptive of the images. For example, the image data 216 can include one or more image files corresponding to the achievement 124, a three-dimensional model corresponding to the achievement 124, and any other data relating to a visual representation of the achievement 124. A first image can correspond to a visual representation of the achievement 124 in an unearned state (e.g., prior to the user fulfilling the requirements of the achievement 124). A second image can correspond to a visual representation of the achievement 124 in an earned state (e.g., after the user has fulfilled the requirements of the achievement 124). The image data 216 together with the achievement text 214 can be used when notifications about the achievement 124 are generated. For example, a first notification may notify the user on the wearable device 106 that she has earned the achievement 124. The first notification can include a three-dimensional visual representation of the achievement 124 based at least in part on the three-dimensional model in the image data. The first notification can also include a string of text based at least in part on the achievement text 214 that informs the user about the achievement 124. Other notifications can include other aspects of the achievement text 214, the image data 216, and/or other data (e.g., sounds, music, spoken words, vibrations, etc.).

The value data 217 can include any suitable value (e.g., a constant number, a computed number based at least in part on an achievement rule, etc.) that can be used when information about the presentation is presented. For example, for an achievement relating to a streak of reaching a movement goal, the value data 217 can correspond to the number of days of the streak. The value data 217 can be generated by evaluating an expression as part of detecting achievements.

The workout type 219 can be included for achievements that relate to workouts. The workout type 219 can indicate the type of workout to which the achievement 124 corresponds. For example, if the achievement 124 corresponds to cycling over 20 miles in one day, the workout type 219 can indicate "cycling" as the workout type in the achievement definition 202.

In some examples, eligibility of earning an achievement may depend on certain aspects of the users of the wearable devices 106 such as country of user, gender of user, region of user, group(s) to which user belongs, and the like. For example, a particular challenge may be specific for female users.

In some examples, eligibility may be based at least in part on performance of a group to which the user belongs. For example, a fitness challenge may be designed that includes a multi-group competition (e.g., one office vs. another office, one country vs. another country, one couple vs. another couple, etc.). Each group can include one or more users. In this manner, the achievement rules for the fitness challenge can be written in a manner that evaluates based at least in part on single users, groups of users, and/or combinations of certain users within the groups. For example, a world-wide steps fitness challenge may be defined and shared with users throughout the world prior to the summer Olympics. Sharing the fitness challenge can include sending a notification about the fitness challenge to wearable devices 106 associated with a defined set of users. The notification can function as an invitation to participate in the fitness challenge. The users can utilize their respective wearable devices 106 to accept or decline the invitation. Thus, instead of invitations getting lost in email or requiring the users to access a webpage, the users can simply and easily join the fitness challenge at their respective wearable devices 106.

The steps challenge may be defined to have groups of users in each participating country compete against each other to see who can record the most steps (e.g., as tracked by the wearable device 106). For example, all users in the United States can together compete against all users in Canada, the United Kingdom, Mexico, and so forth to walk the most steps during the weeks of the Olympic games. As part of the challenge, the users may be presented with a notification about an option to opt-in to the challenge, or in some examples, may automatically be opted in. Opting in may mean that the users agree to share their evaluation data relating to the challenge (e.g., number of steps for each evaluation period and/or other user data).

Information about the challenge may be presented as notifications (e.g., pop-ups, full screen displays, etc.) on the wearable device 106. For example, weeks prior to commencement of the challenge, a notification may be provided to all eligible users in each of the countries. The notification may be sent directly to the eligible users' wearable devices 106. The notification may include information about the challenge, include the opt-in request, and the like. In some examples, at least some of the notifications described herein may be generated locally on the wearable device 106 (e.g., at a fitness application of the wearable device 106) and presented at the wearable device 106.

In some examples, notifications may also be generated based on trigger information. Continuing from the example above, 90 days before the Olympics, a notification may be sent out to initiate the fitness challenge. The notification may be sent out in response to detection of a particular trigger event. In this manner, the trigger event may be used for initiating a fitness challenge via a notification.

In some examples, notifications including status updates may be provided as the user participates in the challenge. For example, in a challenge requiring a user to meet a fitness goal on 75/100 days, a notification may be sent at day 25 that informs the user they she met the fitness goal on 15 days and is still eligible to receive the achievement (e.g., 75 days remain in the challenge period and she only needs to meet the fitness goal on 60 more days). Another notification may be sent at day 90 that informs the user that, because she has only met the fitness goal on 60 days, she is no longer eligible to receive the achievement (e.g., 10 days remain in the challenge period and because she needs 15 total days to reach the 75/100 threshold, she is mathematically eliminated from earning the achievement).

In some examples, processing of the evaluation rules may be performed at the service provider 104 and/or at the user devices. For example, in the user group vs. user group example, the wearable devices 106 may identify the trigger events, and the evaluation rules at the wearable devices 106 may indicate that the wearable devices 106 share certain data with the service provider 104. The service provider 104 may aggregate the data from each of the wearable devices 106 (e.g., of the United States) and compare against the data from other wearable devices 106 of other user groups (e.g., of Canada, the United Kingdom, Mexico, etc.). In addition, the aggregated data can be provided to the wearable devices 106 and/or presented on a webpage in a form of a leaderboard. In some examples, the data from the user groups may be compared on a percentage basis. This may ensure that even small user groups (e.g., small countries) can compete against larger user groups (e.g., large countries).

Figure 3:
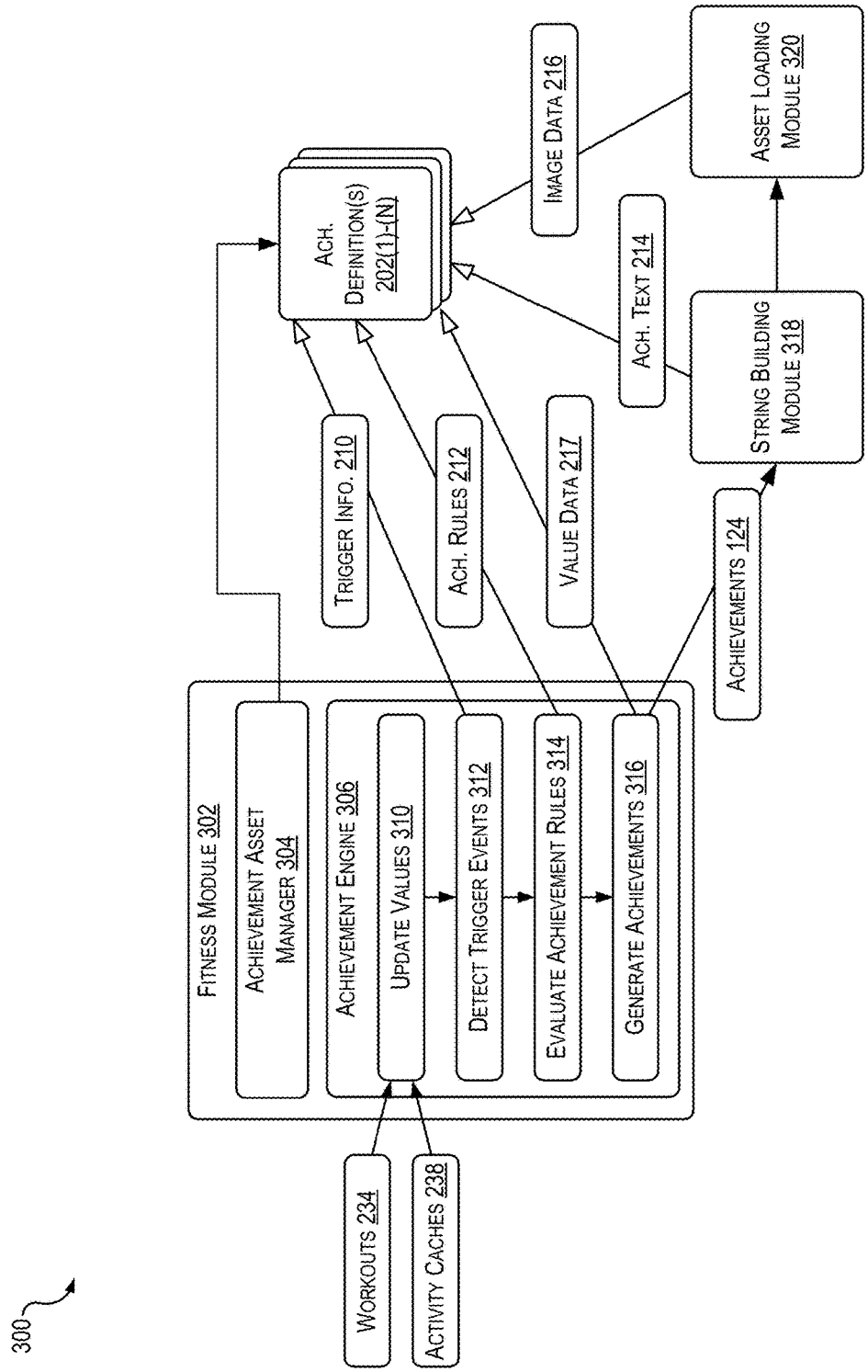
FIG. 3 illustrates a simplified block diagram depicting aspects and functions of a fitness module for managing presentation of achievements as described herein, according to at least one example.

FIG. 3 illustrates a simplified block diagram 300 depicting aspects and functions of a fitness module 302 for use in implementing techniques relating to managing presentation of achievements, according to at least one example. The fitness module 302 can be implemented using the wearable device 106 and/or the electronic device 108 and can be configured to perform the techniques relating to managing presentation of achievements, as described herein. The fitness module 302 can include an achievement asset manager 304 and an achievement engine 306. In some examples, the fitness module 302 may be included in a fitness application.

The achievement asset manager 304 can be configured to manage achievement definitions 202(1)-(*n*) that have been downloaded to the wearable device 106 and/or the electronic device 108. In some examples, the wearable device 106 and/or the electronic device 108 are in communication with the service provider 104 via one or more networks, and the achievement definitions 202(1)-(*n*) are downloaded over the one or more networks. In some examples, as described herein, the service provider 104 can include a mobile asset manager that can be used to send information (e.g., the achievement definitions 202 in one or more asset packages) from the service provider 104 to the achievement asset manager 304. Portions of the achievement definitions 202 can be downloaded in the same or different asset packages. The achievement asset manager 304 may also be configured to manage storage of the achievement definitions 202 at the wearable device 106 and/or the electronic device 108 and manage removal of the achievement definitions 202 from the wearable device 106 and/or the electronic device 108. For example, when an achievement is no longer achievable (e.g., a corresponding fitness challenge has ended), the achievement asset manager 304 can remove the achievement definition corresponding to the achievement. This can free up space on the wearable device 106 and/or the electronic device 108 and also remove the possibility of allocating computing resources to evaluating achievement rules for unachievable achievements.

The achievement engine 306 can receive evaluation data in the form of the workouts 234, the activity caches 238, and the like from those systems of the wearable device 106 and/or the electronic device 108 that are collecting and/or managing the evaluation data. In some examples, the workouts 234 and the activity caches 238 have been generated based at least in part on raw fitness data collected and managed by the other systems. The achievement engine 306 can then use the workouts 234, the activity caches 238, and the like to update values at 310. Updating values 310 can include updating counters to track achievement criteria. For example, if a user had an exercise goal of 30 minutes in one day, the achievement engine 306 can constantly be updating an exercise minute counter relating to the exercise goal for the day using the activity cache 238. The activity cache 238 can be updated according to some fixed interval, in response to events, and the like. For example, the activity cache 238 may be updated more often when the user is wearing the wearable device 106 and working out, as compared to when the user is wearing the wearable device 106 and sleeping. As an additional example, when the wearable device 106 records that a workout has been saved, the workouts 234 will be updated and provided to the achievement engine 306. The achievement engine 306 at 310 can update a value corresponding to the workout.

The values updated at 310 can be used in connection with the trigger information 210 defined by the achievement definitions 202 to determine whether the value and/or other fitness data results in detection of trigger events at 312. Continuing with the example from above, once the values corresponding to daily workout minutes goes from below 30 (e.g., 27) to above 30 (e.g., 31), a trigger event may be detected that corresponds to this information. This is an example of the exercise fitness goal event 222 that may be reflected in the trigger information 210. Similarly, continuing with the additional example from above, once the workouts 234 have been received by the achievement engine 306, a trigger event may be detected that corresponds to the new workout. This is an example of the workout event 230 that may be reflected in the trigger information 210.

Once a trigger event is detected at 312, the achievement engine 306 uses the detected trigger event to identify which achievement rules 212 to evaluate by reviewing the achievement definitions 202(1)-(n). This is possible because each detected trigger event can correspond to at least one achievement rule 212. In some examples, detection of one trigger event can result in the evaluation of one or more achievement rules 212 corresponding to one or more achievement definitions 202. The achievement engine 306 then evaluates the achievement rules at 314 that correspond to the detected trigger event. This can include looping through and evaluating the achievement rules 212 for more than one achievement definition 202 but advantageously not all definitions.

The evaluation at 314 may dictate whether or not achievements are generated at 316. For example, if the evaluation of particular achievement rules 212 for a particular achievement definition 202 is true, then a particular achievement 124 may be generated at 316. This can include checking the value data 217 from the achievement definition 202. Generating the achievements 124 can include sending communications about the achievements 124 to one or more other modules in order to build different pieces of the achievement 124. For example, in response to receiving a communication about the achievement 124, a string building module 318 can access the achievement text 214 from the achievement definition 202 and generate the appropriate text (e.g., a title and description of the achievement) to display with the achievement 124. At or around the same time, in response to receiving a communication about the achievement 124, an asset loading module 320 can access the image data 216 from the achievement definition 202 and generate the appropriate image to display with the text and the achievement 124. In some examples, the string building module 318 and/or the asset loading module 320 are submodules of the achievement engine 306. In some examples, the asset loading module 320 can be used to display the achievement 124 on a display of one of the wearable device 106 and/or the electronic device 108.

Figure 4:
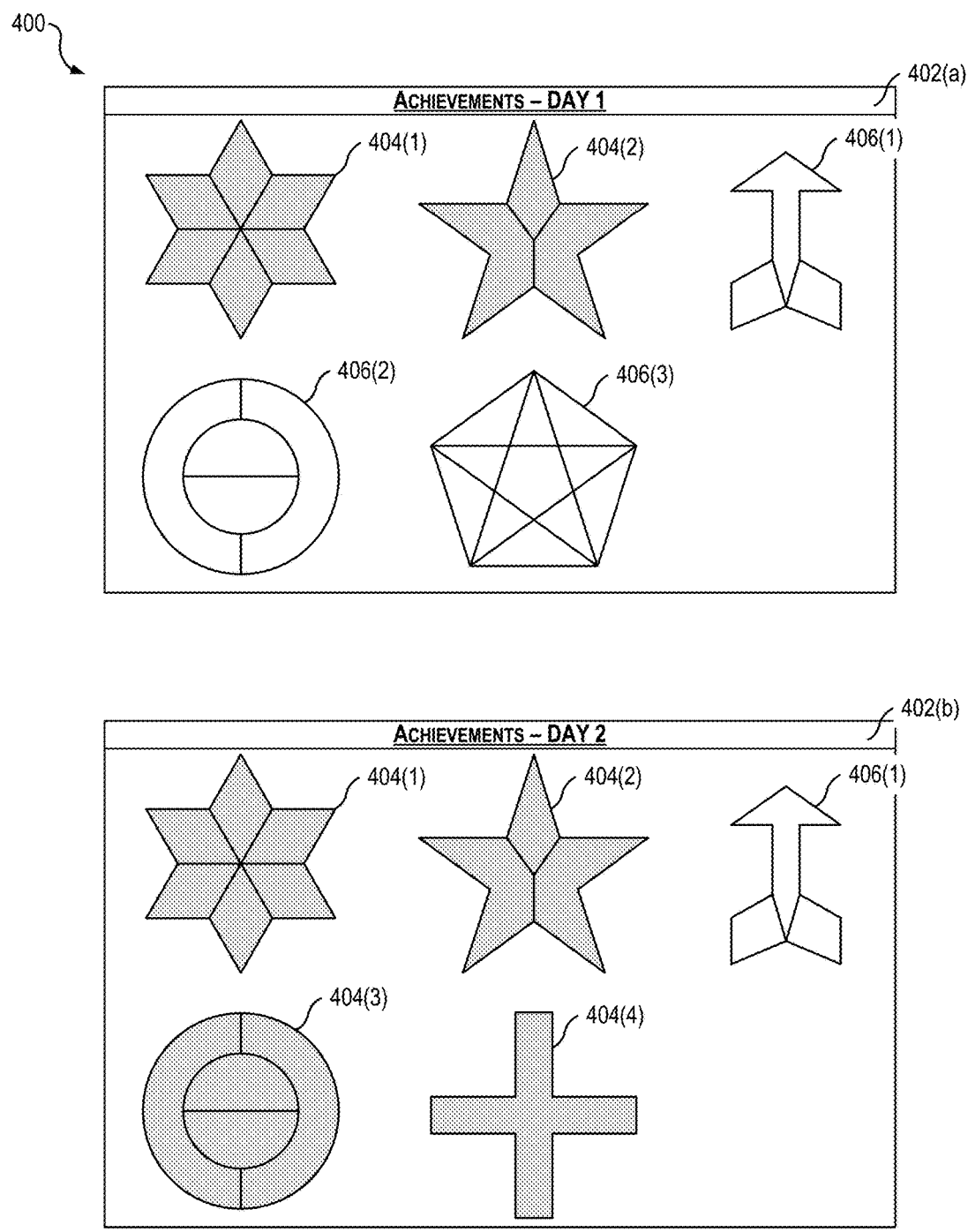
FIG. 4 illustrates an example user interface depicting aspects of an achievement dashboard for managing presentation of achievements as described herein, according to at least one example.

FIG. 4 illustrates an example user interface 400 depicting aspects of an achievement dashboard view 402 for managing presentation of achievements, according to at least one example. The user interface 400 can be used to present the achievement dashboard view 402 on a display of the wearable device 106 and/or the electronic device 108. The dashboard view 402 can be accessed, for example, as a view in a fitness application running on the wearable device 106 and/or the electronic device 108. The dashboard view 402 can represent a digital (e.g., virtual) trophy case where fitness achievement graphical elements can be stored and displayed. These graphical elements are visible representations of the achievement awards. To this end, the dashboard view 402 can include one or more earned achievements 404(1)-(n) and one or more unearned-visible achievements 406(1)-(n). The earned achievements 404 are those achievements that have been earned by the user as described herein. The earned achievements 404 may be presented as color images with enhanced graphical details (e.g., different colors, sparkles, etc.). The unearned-visible achievements 406 are those achievements that the user has not yet earned, but are available to be earned or will be available at some future time. The unearned-visible achievements 406 may be presented in a manner that distinguishes them from the earned achievements 404. For example, the unearned-visible achievements 406 may be presented as a simplified version of the color images (e.g., a line drawing or a grayed-out image). Once a particular unearned-visible achievement 406 is earned, the image corresponding to the particular unearned-visible achievement 406 may be changed (e.g., to a color image). In this manner, the user can visually track which achievements are earned and which are available for being earned. The earned achievements 404 and the unearned-visible achievements 406 may be examples of the achievement 124.

The achievement dashboard view 402(a) corresponds to a first time period and the achievement dashboard view 402(b) corresponds to a second, later time period. Between the two time periods, the wearable device 106 has collected evaluation data, evaluated the evaluation data, and determined whether to generate achievements, remove achievements, and/or change the state of an achievement from unearned to earned.

In some examples, unearned-visible achievements 406 may be added to the dashboard view 402 prior to them actually being available to be earned. For example, as part of a future fitness challenge, a new achievement may be defined. The achievement definition may indicate a visibility date for the achievement, an available-for-earning date, and a challenge-end date. At or around the visibility data, a simplified image (e.g., the line drawing of the unearned-visible achievement 406(2)) corresponding to this achievement may be added to the dashboard view 402, and a notification may be provided to the wearable device 106 and/or the electronic device 108 informing the user of the new challenge. This may allow the user to prepare and/or plan to earn the achievement. Once the available-for-earning date has arrived, the user may be able to earn the achievement 406(2). Once earned, the unearned-visible achievement 406(2) displayed in the achievement dashboard view 402(a) is displayed (at a later time) as the earned achievement 404(3) in the achievement dashboard view 402(b).

In some examples, unearned-visible achievements 406 are removed from the dashboard view 402 if a challenge-end date or other end date has passed (e.g., an achievement relating to meeting a fitness goal in April 2016 and the current data is May 1, 2016). For example, the unearned-visible achievement 406(3) is displayed in the dashboard view 402(a), but at a later time, as shown in the achievement dashboard view 402(b), the unearned-visible achievement 406(3) has been removed. This may because the user has earned the achievement corresponding to the earned achievement 404(4).

In some examples, earned achievements 404 are presented without first being shown in their unearned-visible states. For example, the earned achievement 404(4) is missing from the achievement dashboard view 402(a), but has been added to the achievement dashboard view 402(b).

Aspects of how and when the achievements are displayed in the achievement dashboard may be controlled by the achievement rules. For example, an achievement rule may indicate when to show as visible in an unearned state. Another achievement rule may indicate when the achievement is available.

In a particular example, on May 1, a challenge may be established for earning an achievement for cycling a certain number of miles during the weeks (e.g., July 2 to July 24) while the Tour de France is ongoing. In order to promote the challenge on May 1, a new achievement image may be presented in the achievement dashboard view 402 in an unearned state, and a notification about the challenge can be sent to the wearable device 106 and/or the electronic device 108. A first achievement rule may indicate that the achievement is unavailable, unearned, and visible between May 1 and July 2. This means that the achievement can be displayed in the achievement dashboard view 402 in an unearned-visible state from May 1-July 24. A second achievement rule may indicate that the achievement is available between July 2 and July 24. This means that from July 2-July 24, it is possible for the user to earn the achievement. A third achievement rule may be used to evaluate whether the user has actually achieved the achievement during July 2 to July 24. If yes, the achievement will change the achievement dashboard view 402 to the earned state. After July 24, because the achievement may be unavailable, if it was not earned by the user, it can be removed from the achievement dashboard view 402, e.g., by using another achievement rule.

Figure 5:
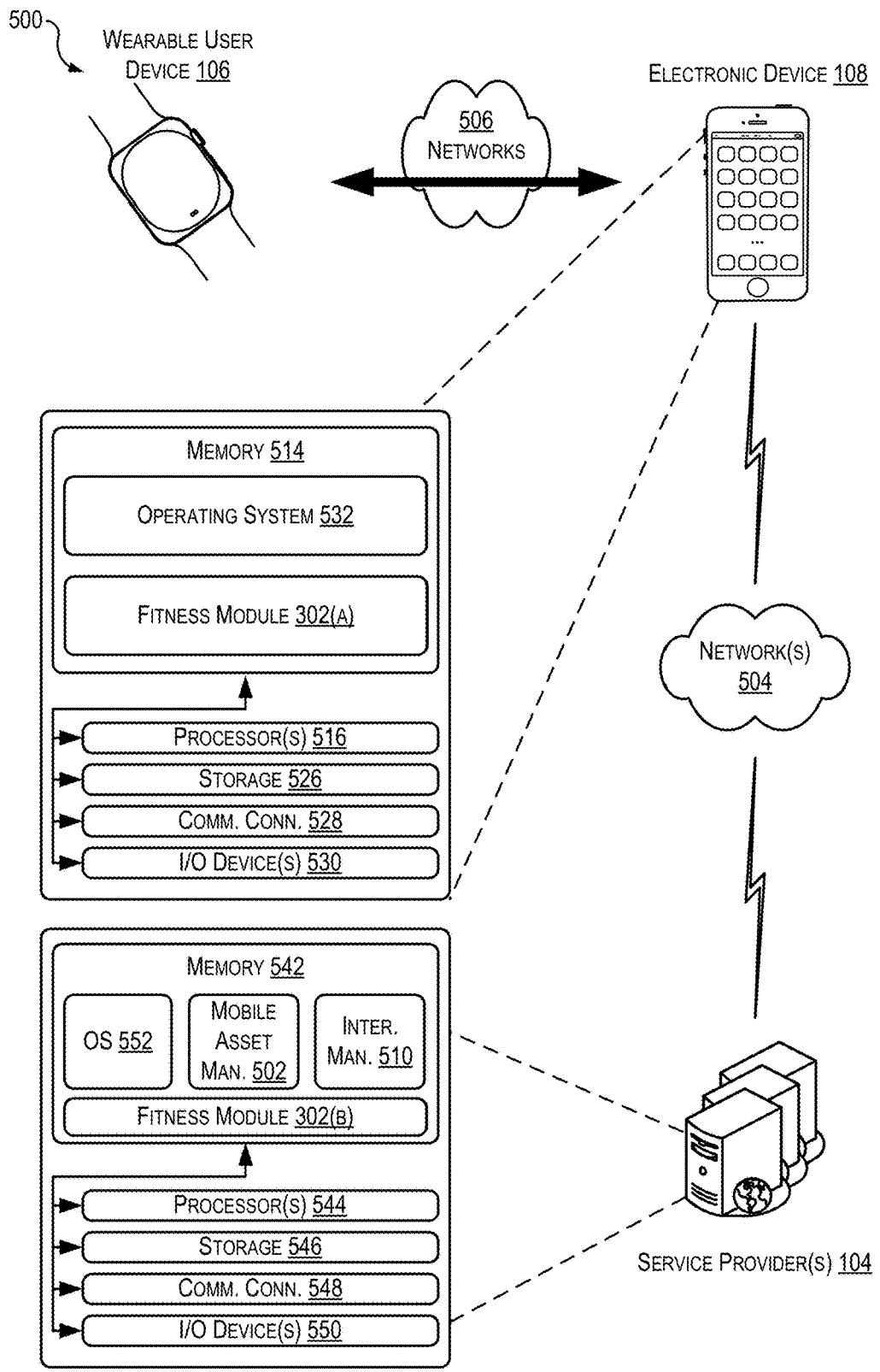
FIG. 5 illustrates a simplified block diagram including an example architecture for managing presentation of achievements as described herein, according to at least one example.

FIG. 5 illustrates an example architecture or environment 500 configured to implement techniques relating to managing presentation of achievements, according to at least one example. In some examples, the example architecture 500 may further be configured to manage or otherwise interact with the wearable device 106, the electronic device 108, and/or the service provider computers 104. In some examples, the devices may be connected via one or more networks 504 and/or 506 (e.g., via Bluetooth, WiFi, the Internet, or the like). In the architecture 500, one or more users may utilize the electronic device 108 to manage, control, or otherwise utilize the wearable device 106, via the one or more networks 506. Additionally, in some examples, the wearable device 106, the service provider computers 104, and the electronic device 108 may be configured or otherwise built as a single device. For example, the wearable device 106 and/or the electronic device 108 may be configured to implement the embodiments described herein as a single computing unit, exercising the examples described above and below without the need for the other devices described.

In some examples, the networks 504, 506 may include any one or a combination of many different types of networks, such as cable networks, the Internet, wireless networks, cellular networks, satellite networks, other private and/or public networks, or any combination thereof. While the illustrated example represents the electronic device 108 accessing the service provider computers 104 via the networks 504, the described techniques may equally apply in instances where the electronic device 108 interacts with the service provider computers 104 over a landline phone, via a kiosk, or in any other manner. It is also noted that the described techniques may apply in other client/server arrangements (e.g., set-top boxes, etc.), as well as in non-client/server arrangements (e.g., locally stored applications, peer to peer configurations, etc.). The wearable device 106 can also access the service provider computers 104 via the networks 504 via the electronic device 108 (e.g., acting as a proxy) or directly.

As noted above, the electronic device 108 may be configured to collect and/or manage user activity data potentially received from the wearable device 106. In some examples, the wearable device 106 may be configured to provide health, fitness, activity, and/or medical data of the user to a third- or first-party application (e.g., the service provider 104). In turn, this data may be used by the electronic device 108 and/or the wearable device 106 to perform the techniques as described herein. The electronic device 108 may be any type of computing device such as, but not limited to, a mobile phone, a smartphone, a personal digital assistant (PDA), a laptop computer, a desktop computer, a thin-client device, a tablet computer, a wearable device, or the like. In some examples, the electronic device 108 may be in communication with the service provider computers 104 and/or the wearable device 106 via the networks 504, 506, or via other network connections.

In one illustrative configuration, the electronic device 108 may include at least one memory 514 and one or more processing units (or processor(s)) 516. The processor(s) 516 may be implemented as appropriate in hardware, computer-executable instructions, firmware, or combinations thereof. Computer-executable instruction or firmware implementations of the processor(s) 516 may include computer-executable or machine-executable instructions written in any suitable programming language to perform the various functions described. The electronic device 108 may also include geo-location devices (e.g., a global positioning system (GPS) device or the like) for providing and/or recording geographic location information associated with the electronic device 108.

The memory 514 may store program instructions that are loadable and executable on the processor(s) 516, as well as data generated during the execution of these programs. Depending on the configuration and type of the electronic device 108, the memory 514 may be volatile (such as random access memory (RAM)) and/or non-volatile (such as read-only memory (ROM), flash memory, etc.). The electronic device 108 may also include additional removable storage and/or non-removable storage 526 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 514 may include multiple different types of memory, such as static random access memory (SRAM), dynamic random access memory (DRAM), or ROM. While the volatile memory described herein may be referred to as RAM, any volatile memory that would not maintain data stored therein once unplugged from a host and/or power would be appropriate.

The memory 514 and the additional storage 526, both removable and non-removable, are all examples of non-transitory computer-readable storage media. For example, non-transitory computer readable storage media may include volatile or non-volatile, removable or non-removable media implemented in any method or technology for storage of information such as computer-readable instructions, data structures, program modules, or other data. The memory 514 and the additional storage 526 are both examples of non-transitory computer storage media. Additional types of computer storage media that may be present in the electronic device 108 may include, but are not limited to, phase-change RAM (PRAM), SRAM, DRAM, RAM, ROM, electrically erasable programmable read-only memory (EEPROM), flash memory or other memory technology, compact disc read-only memory (CD-ROM), digital video disc (DVD) or other optical storage, magnetic cassettes, magnetic tape, magnetic disk storage or other magnetic storage devices, or any other medium that can be used to store the desired information and that can be accessed by the electronic device 108. Combinations of any of the above should also be included within the scope of non-transitory computer-readable storage media. Alternatively, computer-readable communication media may include computer-readable instructions, program modules, or other data transmitted within a data signal, such as a carrier wave, or other transmission. However, as used herein, computer-readable storage media does not include computer-readable communication media.

The electronic device 108 may also contain communications connection(s) 528 that allow the electronic device 108 to communicate with a data store, another computing device or server, user terminals, and/or other devices via the networks 504, 506. The electronic device 108 may also include I/O device(s) 530, such as a keyboard, a mouse, a pen, a voice input device, a touch input device, a display, speakers, a printer, etc.

Turning to the contents of the memory 514 in more detail, the memory 514 may include an operating system 532 and/or one or more application programs or services for implementing the features disclosed herein including the fitness module 302(*a*). As described in detail with reference to later figures, the wearable device 106 may include a memory that includes a similar fitness module 302(*a*), which may be accessible by one or more processors of the wearable device 106. In this manner, the techniques described herein may be implemented by any one, or a combination of more than one, of the computing devices (e.g., the wearable device 106, the electronic device 108, or the service provider 104).

The service provider computers 104 may also be any type of computing device such as, but not limited to, a mobile phone, a smartphone, a PDA, a laptop computer, a desktop computer, a thin-client device, a tablet computer, a wearable device, etc. In some examples, the service provider computers 104 may be in communication with the electronic device 108 and/or wearable device 106 via the networks 504, 506, or via other network connections.

In one illustrative configuration, the service provider computers 104 may include at least one memory 542 and one or more processing units (or processor(s)) 544. The processor(s) 544 may be implemented as appropriate in hardware, computer-executable instructions, firmware, or combinations thereof. Computer-executable instruction or firmware implementations of the processor(s) 544 may include computer-executable or machine-executable instructions written in any suitable programming language to perform the various functions described.

The memory 542 may store program instructions that are loadable and executable on the processor(s) 544, as well as data generated during the execution of these programs. Depending on the configuration and type of service provider computer 104, the memory 542 may be volatile (such as RAM) and/or non-volatile (such as ROM, flash memory, etc.). The service provider computer 104 may also include additional removable storage and/or non-removable storage 546 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 542 may include multiple different types of memory, such as SRAM, DRAM, or ROM. While the volatile memory described herein may be referred to as RAM, any volatile memory that would not maintain data stored therein once unplugged from a host and/or power would be appropriate. The memory 542 and the additional storage 546, both removable and non-removable, are both additional examples of non-transitory computer-readable storage media.

The service provider computer 104 may also contain communications connection(s) 548 that allow the service provider computer 104 to communicate with a data store, another computing device or server, user terminals and/or other devices via the networks 504, 506. The service provider computer 104 may also include I/O device(s) 550, such as a keyboard, a mouse, a pen, a voice input device, a touch input device, a display, speakers, a printer, etc.

Turning to the contents of the memory 542 in more detail, the memory 542 may include an operating system 552 and/or one or more application programs or services for implementing the features disclosed herein including the mobile asset manager 502, an interface manager 510, and the fitness module 302(*b*). In some examples, the mobile asset manager 502 may be configured to manage sending asset packages including achievement definitions to the wearable device 106 and/or the electronic device 108, as described herein. The interface manager 510 may be configured to provide one or more user interfaces for interacting with the service provider 104. For example, the interface manager 510 can present the achievement editor interface described herein.

Figure 6:
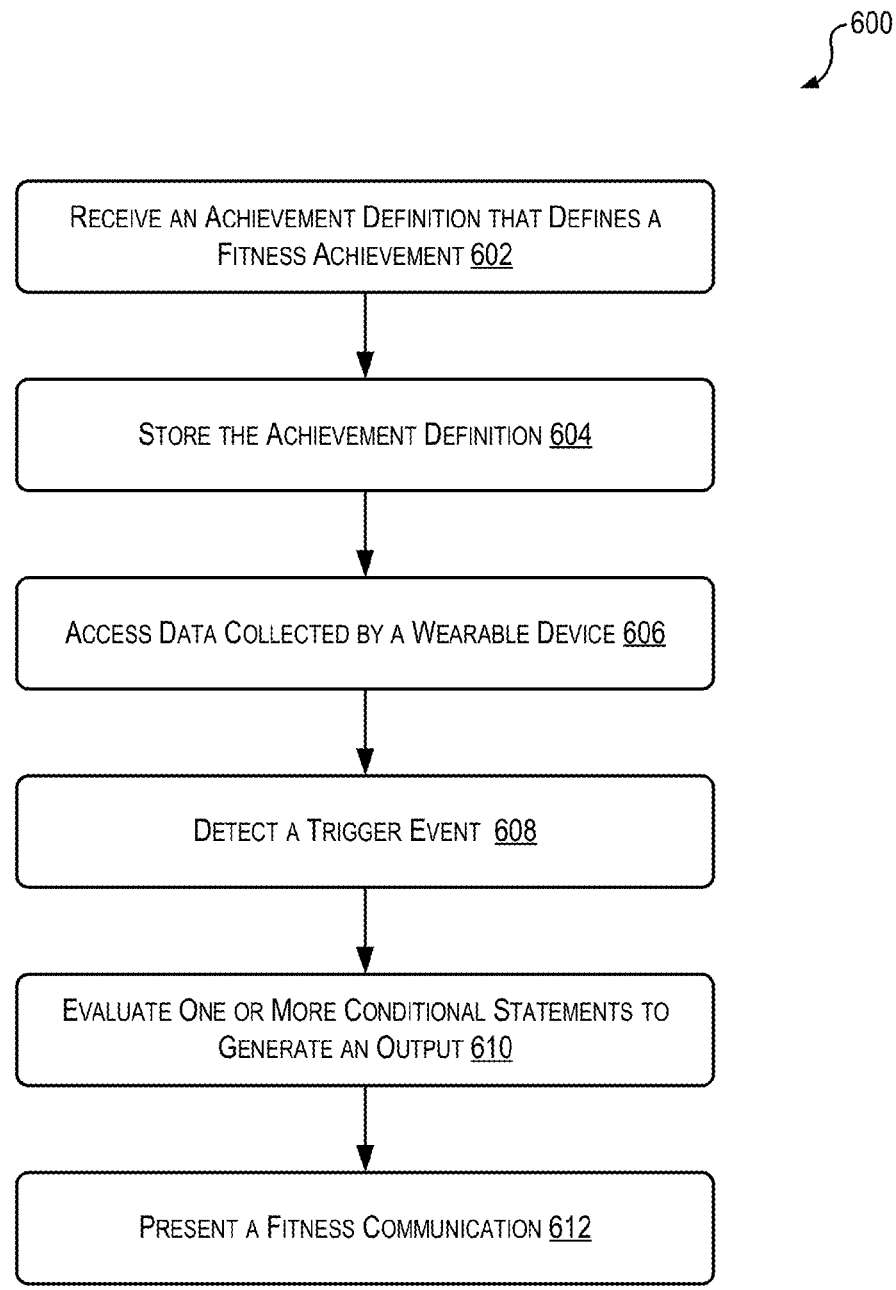
FIG. 6 illustrates a flowchart of a method of managing presentation of achievements as described herein, according to at least one example.
Figure 7:
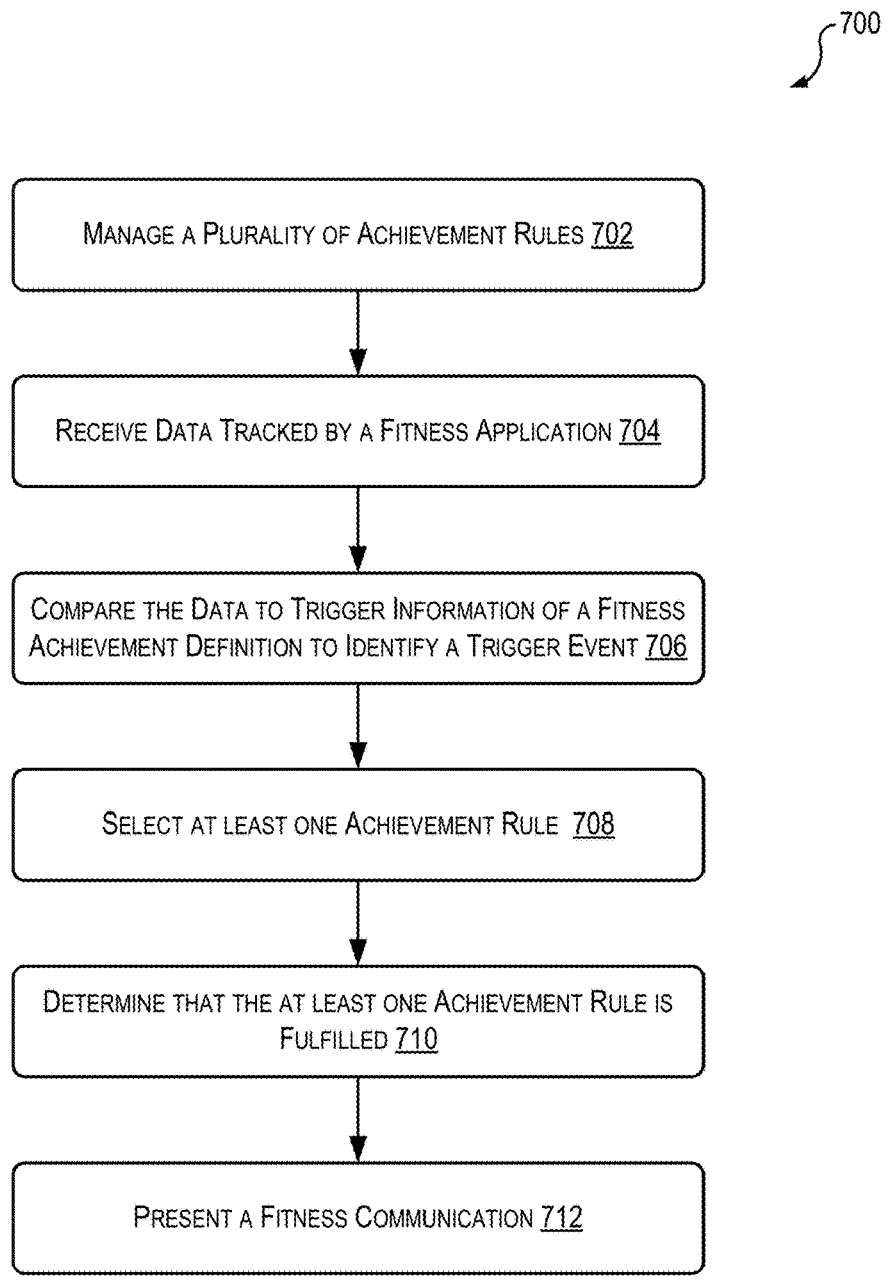
FIG. 7 illustrates a flowchart of a method of managing presentation of achievements as described herein, according to at least one example.

FIGS. 6 and 7 illustrate example flow diagrams showing processes 600 and 700 for managing presentation of achievements, according to at least a few examples. These processes, and any other processes described herein, are illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures and the like that perform particular functions or implement particular data types. The order in which the operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer-readable storage medium, for example, in the form of a computer program including a plurality of instructions executable by one or more processors.

FIG. 6 depicts the process 600 including example acts or techniques for managing presentation of achievements, according to at least one example. The fitness module 302, whether embodied in the wearable device 106, the electronic device 108, or the service provider 104, or any suitable combination of the foregoing may perform the process 600 of FIG. 6. The process 600 begins at 602 by receiving an achievement definition that defines a fitness achievement. In some examples, a fitness application of a wearable device receives the achievement definition. The achievement definition can be non-executable and can include trigger information, one or more conditional statements having at least one criteria, image data corresponding to a fitness achievement graphical element, and any other suitable data. In some examples, the image data includes three-dimensional image files, two-dimensional image files, and the like. The image data may also include first versions of image files corresponding to an unearned state and second versions of image files corresponding to an earned state.

At 604, the process 600 stores the achievement definition. For example, the achievement definition may be stored in one or more memory modules of the wearable device. In some examples, storing the achievement definition may also include removing outdated achievements, unearned and unavailable achievements, and the like from the one or more memory modules. Saving the achievement definition may take place without input from a user. For example, the receiving and storing of the achievement definition may take place over the air at times when the wearable device or other user device is connected to a network.

At 606, the process 600 accesses data collected by the wearable device. The data collected by the wearable device includes any suitable evaluation data. For example, the data can include system data or fitness data collected by the wearable device and tracked by the fitness application and any other suitable data.

At 608, the process 600 detects a trigger event. Detecting the trigger event can be based at least in part on a comparison of the trigger information to the data tracked by the fitness application. For example, the trigger information may define the trigger events, and the data may be used to determine when the trigger events are detected. The trigger events can include, for example, a day change event, achievement of a movement fitness goal event, achievement of an exercise fitness goal event, achievement of stand fitness goal event, achievement of a set of fitness goals event, achievement of a fitness goal beyond a certain amount event, and/or completion of a workout event.

At 610, the process 600 evaluates one or more conditional statements to generate an output. In some examples, evaluating the one or more conditional statements may be based at least in response to detecting the trigger event at 608. Evaluating the one or more conditional statements may include evaluating the one or more conditional statements against at least one criteria using the data accessed at 606 or other data tracked by the fitness application. For example, evaluating the one or more conditional statements may be based at least in part on the same data that was used to detect the trigger event and/or other data. For example, system data that identifies a day change (e.g., from January 21 to January 22) may result in a trigger event. Depending on the achievement definition, other data (e.g., fitness data) may then be used to evaluate the one or more conditional statements against the at least one criteria. The output may indicate in a binary manner (e.g., true or false) the results of the evaluation at 610. In some examples, the output may indicate the results of the evaluation with more than two possible answers. For example, under one evaluation, the output may result in a communication about an upcoming fitness challenge. Under another evaluation, the output may result in a communication about a user's status with regards to the fitness challenge. Under yet another evaluation, the output may result in a communication about an achievement relating to the fitness challenge.

At 612, the process 600 presents a fitness communication. In some examples, the fitness communication is presented based at least in part on the output generated at 610. The fitness communication may correspond to the fitness achievement. As described herein, the fitness communication may include a communication relating to an unavailable-unearned fitness achievement (e.g., "Run at least 5K on Thanksgiving next week and earn the Turkey Trot achievement."), a communication relating to an available-unearned fitness achievement (e.g., "Keep going! Just 2K more to earn the Turkey Trot achievement."), a communication relating to an available, earned fitness achievement (e.g., "Great job! You just earned the Turkey Trot achievement."), and any other suitable communication relating to the fitness achievement. In some examples, the fitness communication may include text, images, and the like. In some examples, the fitness communication may be presented on the wearable device and/or the electronic device. The fitness communication may be provided to the wearable device and/or the electronic device as a notification in the form of a pop-up, a full screen notification, or the like. In some examples, the fitness communication may be provided to the wearable device and/or the electronic device as message, which may be accessed through a messaging application. In some examples, the fitness communication may cause presentation of a fitness dashboard in which the fitness graphical element corresponding to the fitness achievement may be presented. For example, the fitness communication may indicate that the fitness achievement is earned, include an image corresponding to the fitness achievement, and a link to the fitness dashboard. In some examples, the fitness dashboard may be accessible via the electronic device.

FIG. 7 depicts the process 700 including example acts or techniques relating to managing presentation of achievements, according to at least one example. The fitness module 302, whether embodied in the wearable device 106, the electronic device 108, or the service provider 104, or any suitable combination of the foregoing may perform the process 700 of FIG. 7. The process 700 begins at 702 by managing a plurality of achievement rules. The plurality of achievement rules may be stored on a user device. In some examples, the plurality of achievement rules may correspond to a plurality of achievement definitions. At least a portion of the plurality of achievement rules may relate to available-unearned achievements. At least a portion of the plurality of achievement rules may relate to unavailable-unearned achievements.

At 704, the process 700 receives data tracked by a fitness application. The fitness application may run on an electronic device. At least a portion of the data may be collected by a separate fitness application running on a wearable device. In some examples, the fitness application at 704 is the same fitness application that collects the data.

At 706, the process 700 compares the data to trigger information of a fitness achievement definition to identify a trigger event. In some examples, the fitness achievement definition may include the trigger information and an achievement rule corresponding to the trigger information. In some examples, the fitness achievement definition may be downloaded to by the user device and stored on the user device prior to 706.

At 708, the process 700 selects at least one achievement rule. In some examples, selecting the at least one achievement rule may be based at least in part on the fitness achievement definition. For example, the fitness achievement definition may define what trigger events correspond to which achievement rules. In some examples, the at least one achievement rule may be selected from a set of achievement rules that includes the plurality of achievement rules managed at 702 the achievement rule associated with the fitness achievement definition. In some examples, the at least one achievement rule is the achievement rule. The achievement rules may include one or more conditional statements including criteria.

At 710, the process 700 determines that the at least one achievement rule is fulfilled. This may include evaluating the at least one achievement rule based at least in part on the data tracked at 704 or other data tracked by the fitness application against criteria included in the achievement rule.

At 712, the process 700 presents a fitness communication. This may be based at least in response to determining that the at least one achievement rule is fulfilled. In some examples, the fitness communication may correspond to the fitness achievement definition as described herein. Presenting the fitness communication may also include presenting a fitness achievement graphical element corresponding to the fitness achievement in an achievement dashboard of the user device or related user device.

Figure 8:
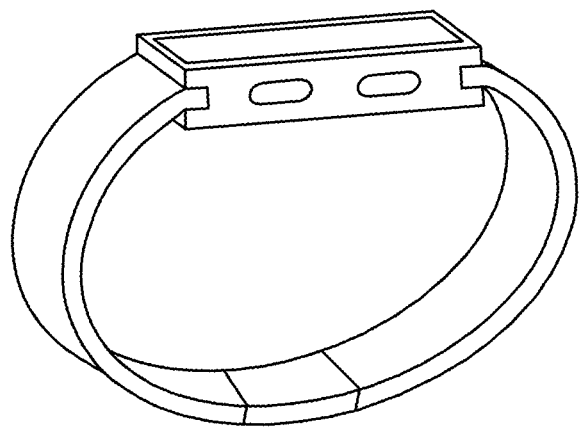
FIG. 8 illustrates an electronic device for managing presentation of achievements as described herein, according to at least one example.

Embodiments described herein may take the form of, be incorporated in, or operate with a suitable electronic device. One example of such a device is shown in FIG. 8 and takes the form of a wearable mechanism. As shown, the mechanism may be worn on a user's wrist and secured thereto by a band. The mechanism may have a variety of functions including, but not limited to: keeping time; monitoring a user's physiological signals and providing health-related information based at least in part on those signals; communicating (in a wired or wireless fashion) with other electronic devices, which may be different types of devices having different functionalities; providing alerts to a user, which may include audio, haptic, visual and/or other sensory output, any or all of which may be synchronized with one another; visually depicting data on a display; gather data form one or more sensors that may be used to initiate, control, or modify operations of the device; determine a location of a touch on a surface of the device and/or an amount of force exerted on the device, and use either or both as input; accepting voice input to control one or more functions; accepting tactile input to control one or more functions; and so on.

Alternative embodiments of suitable electronic devices include a phone; a tablet computing device; a portable media player; and so on. Still other suitable electronic devices may include laptop/notebook computers, personal digital assistants, touch screens, input-sensitive pads or surfaces, and so on.

In some embodiments the electronic device may accept a variety of bands, straps, or other retention mechanisms (collectively, "bands"). These bands may be removably connected to the electronic device by a lug that is accepted in a recess or other aperture within the device and locks thereto. The lug may be part of the band or may be separable (and/or separate) from the band. Generally, the lug may lock into the electronic device's recess and thereby maintain connection between the band and device. The user may release a locking mechanism to permit the lug to slide or otherwise move out of the recess. In some embodiments, the recess may be formed in the band and the lug may be affixed or incorporated into the device.

A user may change combinations of bands and electronic devices, thereby permitting mixing and matching of the two categories. It should be appreciated that devices having other forms and/or functions may include similar recesses and may releasably mate with a lug and/or band incorporating a lug. In this fashion, an ecosystem of bands and devices may be envisioned, each of which is compatible with another. A single band may be used to connect to devices, as one further example; in such embodiments the band may include electrical interconnections that permit the two devices to transmit signals to one another and thereby interact with one another.

In many embodiments, the electronic device may keep and display time, essentially functioning as a wristwatch among other things. Time may be displayed in an analog or digital format, depending on the device, its settings, and (in some cases) a user's preferences. Typically, time is displayed on a digital display stack forming part of the exterior of the device.

The display stack may include a cover element, such as a cover glass, overlying a display. The cover glass need not necessarily be formed from glass, although that is an option; it may be formed from sapphire, zirconia, alumina, chemically strengthened glass, hardened plastic and so on. Likewise, the display may be a liquid crystal display, an organic light-emitting diode display, or any other suitable display technology. Among other elements, the display stack may include a backlight in some embodiments.

The device may also include one or more touch sensors to determine a location of a touch on the cover glass. A touch sensor may be incorporated into or on the display stack in order to determine a location of a touch. The touch sensor may be self-capacitive in certain embodiments, mutual-capacitive in others, or a combination thereof.

Similarly, the device may include a force sensor to determine an amount of force applied to the cover glass. The force sensor may be a capacitive sensor in some embodiments and a strain sensor in other embodiments. In either embodiment, the force sensor is generally transparent and made from transparent materials, or is located beneath or away from the display in order not to interfere with the view of the display. The force sensor may, for example, take the form of two capacitive plates separated by silicone or another deformable material. As the capacitive plates move closer together under an external force, the change in capacitance may be measured and a value of the external force correlated from the capacitance change. Further, by comparing relative capacitance changes from multiple points on the force sensor, or from multiple force sensors, a location or locations at which force is exerted may be determined. In one embodiment the force sensor may take the form of a gasket extending beneath the periphery of the display. The gasket may be segmented or unitary, depending on the embodiment.

The electronic device may also provide alerts to a user. An alert may be generated in response to: a change in status of the device (one example of which is power running low); receipt of information by the device (such as receiving a message); communications between the device and another mechanism/device (such as a second type of device informing the device that a message is waiting or communication is in progress); an operational state of an application (such as, as part of a game, or when a calendar appointment is imminent) or the operating system (such as when the device powers on or shuts down); and so on. The number and types of triggers for an alert are various and far-ranging.

The alert may be auditory, visual, haptic, or a combination thereof. A haptic actuator may be housed within the device and may move linearly to generate haptic output (although in alternative embodiments the haptic actuator may be rotary or any other type). A speaker may provide auditory components of an alert and the aforementioned display may provide visual alert components. In some embodiments a dedicated light, display, or other visual output component may be used as part of an alert.

The auditory, haptic, and/or visual components of the alert may be synchronized to provide an overall experience to a user. One or more components may be delayed relative to other components to create a desired synchronization among them. The components may be synchronized so that they are perceived substantially simultaneously; as one example, a haptic output may be initiated slightly before an auditory output since the haptic output may take longer to be perceived than the audio. As another example, a haptic output (or portion thereof) may be initiated substantially before the auditory output, but at a weak or even subliminal level, thereby priming the wearer to receive the auditory output.

Figure 9:
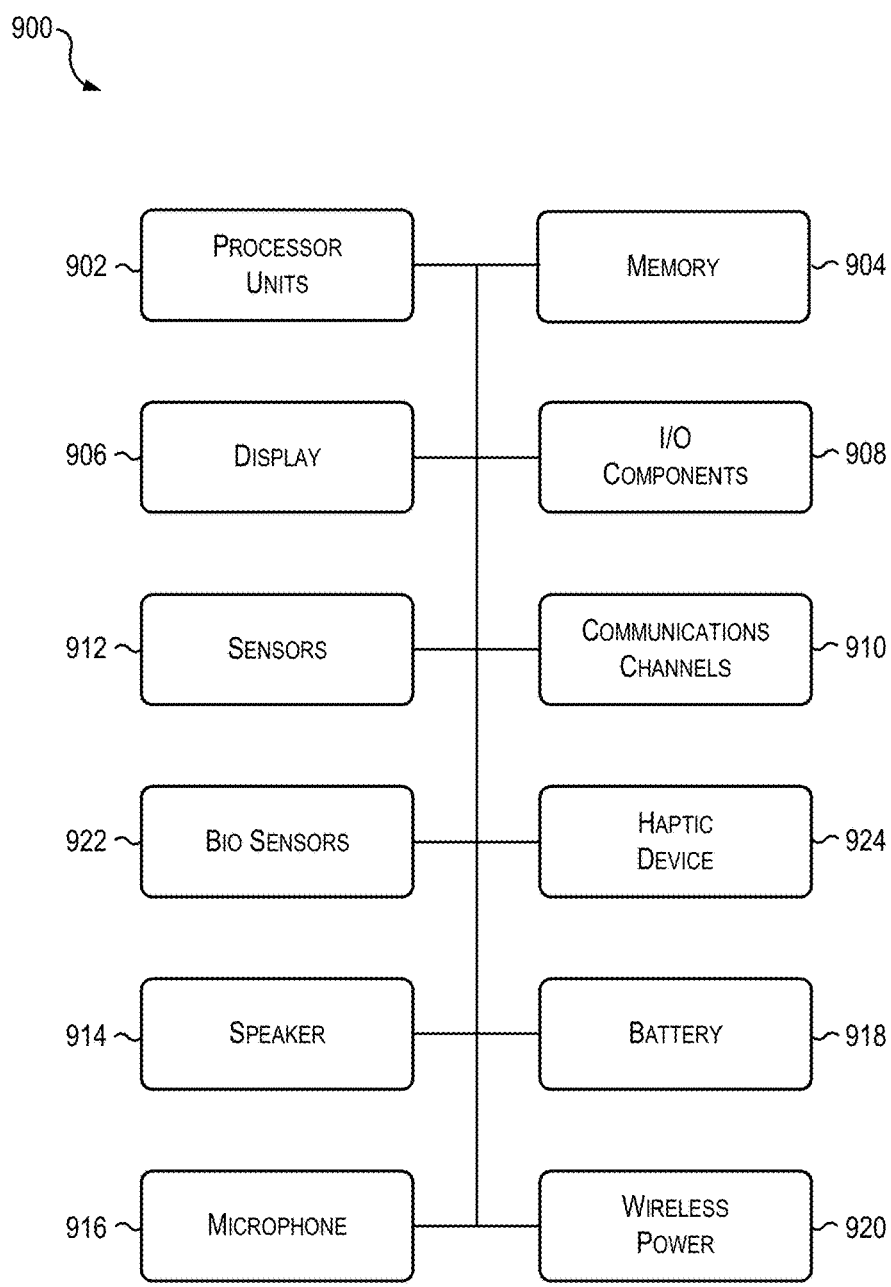
FIG. 9 illustrates a simplified block diagram including components of an example electronic device for managing presentation of achievements as described herein, according to at least one example.

FIG. 9 depicts an example schematic diagram of a wearable electronic device 900. The wearable electronic device 900 is an example of the wearable device 106. As shown in FIG. 9, the device 900 includes one or more processing units 902 that are configured to access a memory 904 having instructions stored thereon. The instructions or computer programs may be configured to perform one or more of the operations or functions described with respect to the device 900 (e.g., the fitness module 3023(c)). For example, the instructions may be configured to control or coordinate the operation of the various components of the device. Such components include, but are not limited to, display 906, one or more input/output components 908, one or more communication channels 910, one or more sensors 912, a speaker 914, microphone 916, a battery 918, wireless power 920, bio sensors 922, and/or one or more haptic feedback devices 924. In some embodiments the speaker and microphone may be combined into a single unit and/or may share a common port through a housing of the device.

The processing units 902 of FIG. 9 may be implemented as any electronic device capable of processing, receiving, or transmitting data or instructions. For example, the processing units 902 may include one or more of: a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements.

Figure 10:
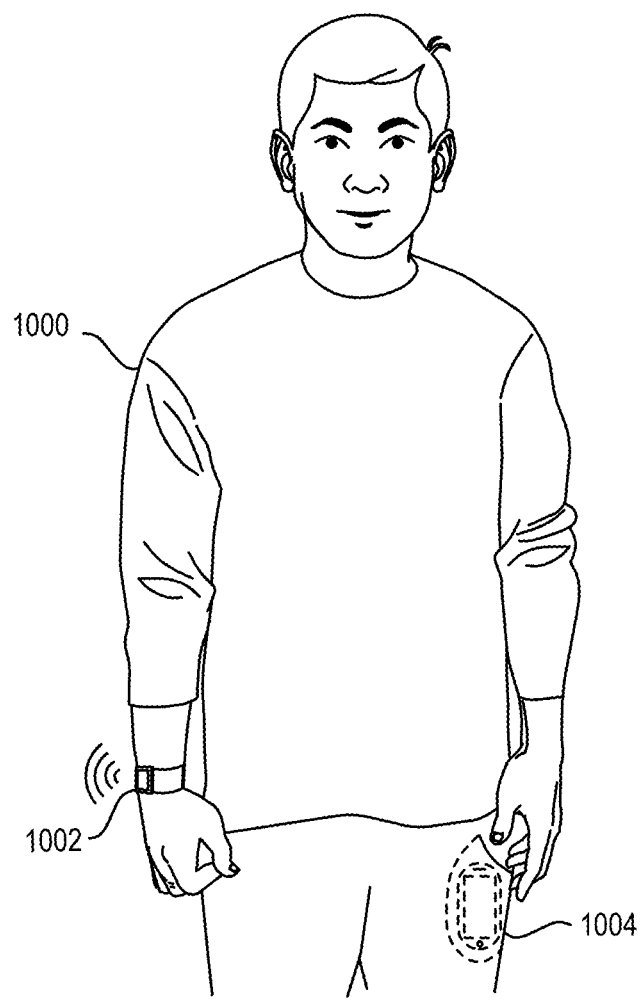
FIG. 10 illustrates a simplified diagram including example electronic devices for managing presentation of achievements as described herein, according to at least one example.

The example electronic device may communicate with other electronic devices either through a wired connection or wirelessly. Data may be passed between devices, permitting one device to relay information to another; control another; employ another's sensors, outputs, and/or inputs; and so on. FIG. 10 depicts a user 1000 wearing a first electronic device 1002 with a second electronic device 1004 in his pocket. Data may be wirelessly transmitted between the electronic devices 1002, 1004, thereby permitting the user 1000 to receive, view, and interact with data from the second device 1004 by means of the first electronic device 1002. Thus, the user 1000 may have access to part or all of the second device's functionality through the first electronic device 1002 without actually needing to interact directly with the second device 1004. In some examples, the second electronic device 1004 may be an example of the electronic device 108. The first electronic device 1002 may be an example of the wearable device 106.

Further, the electronic devices 1002, 1004 may cooperate not only to share data, but to share functionality as well. For example, one of the two devices may incorporate a sensor, application, or function that the other lacks. The electronic device lacking such capabilities may request them from the other device, which may share wirelessly with the requesting device. Thus, multiple devices may operate together to provide expanded functions, software, access, and the like between the two and ultimately to a user. As one non-limiting example, the electronic device 1002 may be unable to place or receive telephone calls while the second device 1004 may be able to do so. A user may nonetheless make and/or receive calls through the first device 1002, which may employ the second device 1004 to actually place or accept a call.

As another non-limiting example, an electronic device 1002 may wirelessly communicate with a sales terminal nearby, thus permitting a user to quickly and efficiently conduct a transaction such as selling, buying, or returning a good. The electronic device may use near field communications technology to perform these and other functions.

As mentioned above, a band may be connected to two electronic devices and may serve as a wired communication path between the two. As another example, the devices may communicate wirelessly, thereby permitting one device to relay information from a second to a user. This latter example may be particularly useful when the second is inaccessible.

Certain embodiments may incorporate one or more biometric sensors to measure certain physiological characteristics of a user. The device may include a photoplesymogram sensor to determine a user's heart rate or blood oxygenation levels, for example. The device may also or instead include electrodes to measure the body impedance of a user, which may permit the device to estimate body fat percentages, the body's electrical activity, body impedance, and so on. Also include blood pressure, ultraviolet exposure, etc. Depending on the sensors incorporated into or associated with the electronic device, a variety of user characteristics may be measured and/or estimated, thereby permitting different health data to be provided to a user. In some examples, the sensed biometric data may be used, in part, to determine the historic, current, and/or predicted activity data of the user.

Certain embodiments may be wirelessly charged. For example, an inductive charging base may transmit power to an inductive receiver within the device in order to charge a battery of the device. Further, by varying the inductive field between the device and base, data may be communicated between the two. As one simple non-limiting example, this may be used to wake the base from a low-power sleep state to an active charging state when the device is placed on the base. Other wireless charging systems may also be used (e.g., near field magnetic resonance and radio frequency). Alternatively, the device may also employ wired charging through electrodes.

In certain embodiments, the device may include a rotary input, which may take the form of a crown with a stem. The crown and stem may be rotated to provide the rotary input. Rotation of the stem and/or crown may be sensed optically, electrically, magnetically, or mechanically. Further, in some embodiments the crown and stem may also move laterally, thereby providing a second type of input to the device.

The electronic device may likewise include one or more buttons. The button(s) may be depressed to provide yet another input to the device. In various embodiments, the button may be a dome switch, rocker switch, electrical contact, magnetic switch, and so on. In some embodiments the button may be waterproof or otherwise sealed against the environment.

Various embodiments may include or otherwise incorporate one or more motion sensors. A motion sensor may detect motion of the device and provide, modify, cease, or otherwise affect a state, output, or input of the device or associated applications based at least in part on the motion. As non-limiting examples, a motion may be used to silence the device or acknowledge an alert generated by the device. Sample motion sensors include accelerometers, gyroscopic sensors, magnetometers, GPS sensors, distance sensors, and so on. Some embodiments may use a GPS sensor to facilitate or enable location and/or navigation assistance.

As shown in FIG. 9, the device 900 may also include one or more acoustic elements, including a speaker 914 and/or a microphone 916. The speaker 914 may include drive electronics or circuitry and may be configured to produce an audible sound or acoustic signal in response to a command or input. Similarly, the microphone 916 may also include drive electronics or circuitry and is configured to receive an audible sound or acoustic signal in response to a command or input. The speaker 914 and the microphone 916 may be acoustically coupled to port or opening in the case that allows acoustic energy to pass, but may prevent the ingress of liquid and other debris.

Certain embodiments may incorporate an ambient light sensor. The ambient light sensor may permit the device to sense a brightness of its environment and adjust certain operational parameters accordingly. For example, the electronic device may modify a brightness of a display in response to the sensed ambient light. As another example, the electronic device may turn the display off if little or no light is sensed for a period of time.

These and other functions, operations, and abilities of the electronic device will be apparent upon reading the specification in its entirety.

Certain embodiments of a wearable electronic device may include one or more sensors that can be used to calculate a health metric or other health-related information. As one example, a wearable electronic device may function as a wearable health assistant that provides health-related information (whether real-time or not) to the user, authorized third parties, and/or an associated monitoring device.

Figure 11:
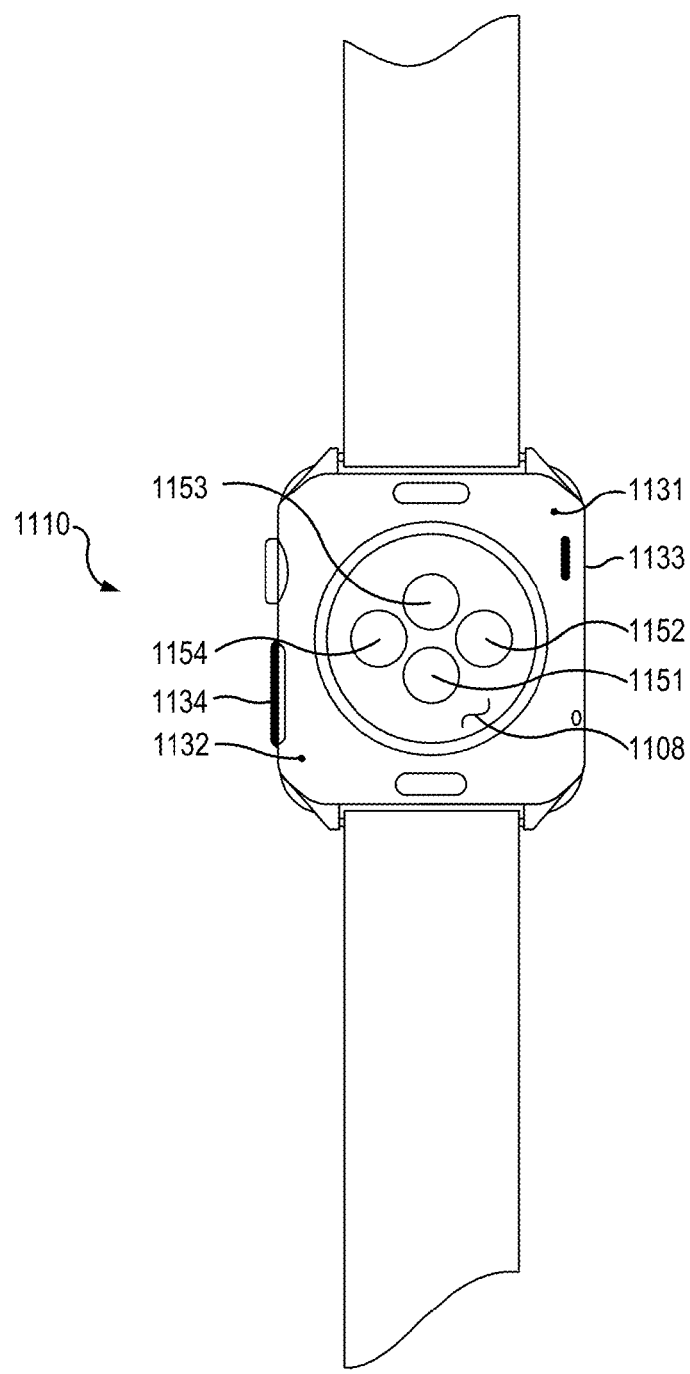
FIG. 11 illustrates an example electronic device for managing presentation of achievements as described herein, according to at least one example.

FIG. 11 depicts an example electronic device 1100 having one or more biometric sensors. The electronic device 1100 is an example of the wearable device 106. As shown in FIG. 11, an array of light sources and a photodetector 1151-1154 may be disposed on the rear surface of the device 1100. In one example, the light sources 1151-1153 are formed from light emitting diode (LED) elements that are configured to emit light into a portion of the wearer's body (e.g., wrist). The photodetector 1154 is shared between the multiple light sources 1151-1153 and is configured to receive light reflected from the body. The photodetector may be formed from a photodiode material that is configured to produce a signal based at least in part on the received light. In one implementation, the signal produced by the photodetector 1154 is used to compute a health metric associated with the wearer. In some cases, the light sources 1151-1153 and the photodetector 1154 form a photoplethysmography (PPG) sensor. The first light source 1151 may include, for example, a green LED, which may be adapted for detecting blood perfusion in the body of the wearer. The second light source 1152 may include, for example, an infrared LED, which may be adapted to detect changes in water content or other properties of the body. The third 1153 light source may be a similar type or different types of LED element, depending on the sensing configuration. The optical (e.g., PPG) sensor or sensors may be used to compute various health metrics, including, without limitation, a heart rate, a respiration rate, blood oxygenation level, a blood volume estimate, blood pressure, or a combination thereof. One or more of the light sources 1151-1153 and the photodetector 1154 may also be used for optical data transfer with a base or other device. While FIG. 11 depicts one example embodiment, the number of light sources and/or photodetectors may vary in different embodiments. For example, another embodiment may use more than one photodetector. Another embodiment may also use fewer or more light sources than are depicted in the example of FIG. 11.

Also as shown in FIG. 11, the device 1100 includes multiple electrodes 1131, 1132, 1133, 1134 that are located on or near external surfaces of the device 1100. In the present example, the device 1100 includes a first electrode 1131 and a second electrode 1132 that are located on or proximate to a rear-facing surface of the device body 1110. In this example, the first electrode 1131 and the second electrode 1132 are configured to make electrical contact with the skin of the user wearing the device 1100. In some cases, the first 1131 and second 1132 electrodes are used to take an electrical measurement or receive an electrical signal from the body of the user. As also shown in FIG. 11, the device 1100 may include a third electrode 1133 and a fourth electrode 1134 that are located on or proximate to a perimeter of the case of the device body 1110. In the present example, the third 1133 and fourth 1134 electrodes are configured to be contacted by one or more fingers of the user who is wearing or interacting with the device 1100. In some cases, the third 1133 and fourth 1134 electrodes are also used to take an electrical measurement or receive an electrical signal from the body of the user. In some cases, the first 1131, second 1132, third 1133, and fourth 1134 electrodes are all used to take a measurement or series of measurements that can be used to compute another health metric of the user's body. Health metrics that may be computed using the electrodes include, without limitation, heart functions (ECG, EKG), water content, body-fat ratios, galvanic skin resistance, and combinations thereof.

In the configuration depicted in FIG. 11, the electronic device 1100 includes one or more apertures in the case 1110.

A light source 1151-1154 may be disposed in each aperture. In one embodiment, each light source 1151-1153 is implemented as a light-emitting diode (LED). In the present example, the four apertures, three light sources 1151-1153, and a single detector 1154 are used to form one or more sensors. Other embodiments can include any number of light sources. For example, two light sources can be used in some embodiments.

The light sources may operate at the same light wavelength range, or the light sources can operate at different light wavelength ranges. As one example, with two light sources one light source may transmit light in the visible wavelength range while the other light source can emit light in the infrared wavelength range. With four light sources, two light sources may transmit light in the visible wavelength range while the other two light sources can emit light in the infrared wavelength range. For example, in one embodiment, at least one light source can emit light in the wavelength range associated with the color green while another light source transmits light in the infrared wavelength range. When a physiological parameter of the user is to be determined, the light sources emit light toward the user's skin and the optical sensor senses an amount of reflected light. In some cases, a modulation pattern or sequence may be used to turn the light sources on and off and sample or sense the reflected light.

As described above, one aspect of the present technology is the gathering and use of data available from various sources to enable users to participate in fitness challenges. The present disclosure contemplates that in some instances, this gathered data may include personal information data that uniquely identifies or can be used to contact or locate a specific person. Such personal information data can include demographic data, location-based data, telephone numbers, email addresses, twitter ID's, home addresses, or any other identifying information. In some instances, such data may include fitness data that identifies aspects actual workouts, calories burned, steps taken, and the like associated with a user.

The present disclosure recognizes that the use of such personal information data and fitness data, in the present technology, can be used to the benefit of users. For example, the fitness data can be used to compare users (or groups of user) to other users (or other groups of users) according to a health or fitness metric. The use of such personal information data enables identification of characteristics of the users that are generated the fitness data. Further, other uses for personal information data that benefit the user are also contemplated by the present disclosure.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of sharing fitness data, the present technology can be configured to allow users to select to "opt in" or "opt out" of participation in the collection of fitness data during registration for services.

Therefore, although the present disclosure broadly covers use of personal information data and fitness data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data and/or fitness data.

Illustrative methods and systems for managing presentation of fitness achievements are described above. Some or all of these systems and methods may, but need not, be implemented at least partially by architectures such as those shown at least in FIGS. 1-11. While many of the embodiments are described above with reference to personal, activity, and/or health-related information, it should be understood that any type of user information or non-user information (e.g., data of any type) may be managed using these techniques. Further, in the foregoing description, various non-limiting examples were described. For purposes of explanation, specific configurations and details are set forth in order to provide a thorough understanding of the examples. However, it should also be apparent to one skilled in the art that the examples may be practiced without the specific details. Furthermore, well-known features were sometimes omitted or simplified in order not to obscure the example being described.

The various embodiments further can be implemented in a wide variety of operating environments, which in some cases can include one or more user computers, computing devices or processing devices which can be used to operate any of a number of applications. User or client devices can include any of a number of general purpose personal computers, such as desktop or laptop computers running a standard operating system, as well as cellular, wireless and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Most embodiments utilize at least one network that would be familiar to those skilled in the art for supporting communications using any of a variety of commercially-available protocols, such as TCP/IP, OSI, FTP, UPnP, NFS, CIFS, and AppleTalk. The network can be, for example, a local area network, a wide-area network, a virtual private network, the Internet, an intranet, an extranet, a public switched telephone network, an infrared network, a wireless network, and any combination thereof.

In embodiments utilizing a network server, the network server can run any of a variety of server or mid-tier applications, including HTTP servers, FTP servers, CGI servers, data servers, Java servers, and business application servers. The server(s) may also be capable of executing programs or scripts in response to requests from user devices, such as by executing one or more applications that may be implemented as one or more scripts or programs written in any programming language, such as Java®, C, C# or C++, or any scripting language, such as Perl, Python or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network (SAN) familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as RAM or ROM, as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a non-transitory computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Non-transitory storage media and computer-readable media for containing code, or portions of code, can include any appropriate media known or used in the art, including storage media, such as, but not limited to, volatile and non-volatile, removable and non-removable media implemented in any method or technology for storage of information such as computer-readable instructions, data structures, program modules, or other data, including RAM, ROM, Electrically Erasable Programmable Read-Only Memory (EEPROM), flash memory or other memory technology, CD-ROM, DVD or other optical storage, magnetic cassettes, magnetic tape, magnetic disk storage or other magnetic storage devices, or any other medium which can be used to store the desired information and which can be accessed by a system device. Based at least in part on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (e.g., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A computer-implemented method, comprising:
receiving, by a fitness application of a wearable device, a non-executable fitness achievement definition that defines a fitness achievement, the non-executable fitness achievement definition comprising:
trigger information identifying one or more trigger events that occur independent of fulfillment of the fitness achievement;
one or more conditional statements having at least one criteria corresponding to the fitness achievement, evaluation of the one or more conditional statements triggered by detecting the one or more trigger events; and
image data corresponding to a fitness achievement graphical element that is specific to the fitness achievement;
storing the non-executable fitness achievement definition on the wearable device;
accessing, by the fitness application, data tracked by the fitness application and collected by the wearable device, at least a portion of the data comprising fitness data;
detecting a trigger event of the one or more trigger events based at least in part on a comparison of the trigger information to the data tracked by the fitness application;
responsive to detecting the trigger event, evaluating the one or more conditional statements against the at least one criteria using one or more of the data or other data tracked by the fitness application to generate an output; and
presenting, based at least in part on the output, a fitness communication on the wearable device, the fitness communication corresponding to the fitness achievement.

2. The computer-implemented method of claim 1, wherein the fitness communication comprises a notification of a future fitness challenge in which the fitness achievement can be earned.

3. The computer-implemented method of claim 1, wherein the fitness communication comprises the fitness achievement graphical element corresponding to the fitness achievement and a notification that the fitness achievement has been earned.

4. The computer-implemented method of claim 1, further comprising, in response to evaluating the one or more conditional statements to generate the output, presenting the fitness achievement graphical element in a view of a second fitness application on a mobile device, the view comprising at least one other fitness achievement graphical element corresponding to a preexisting fitness achievement.

5. The computer-implemented method of claim 1, wherein the trigger event comprises at least one of: a day change event, achievement of a movement fitness goal event, achievement of an exercise fitness goal event, achievement of stand fitness goal event, achievement of a set of fitness goals event, achievement of a fitness goal beyond a certain amount event, or completion of a workout event.

6. A computer-implemented method, comprising:
receiving, by a fitness application of a user device, a fitness achievement definition that defines a fitness achievement, the fitness achievement definition comprising:
trigger information identifying one or more trigger events that occur independent of fulfillment of the fitness achievement; and
one or more conditional statements having at least one fitness achievement criteria, evaluation of the one or more conditional statements triggered by detecting the one or more trigger events;
storing the fitness achievement definition on the user device;
managing a plurality of conditional statements previously stored on the user device;
comparing the trigger information to data tracked by the fitness application to detect a trigger event of the one or more trigger events;
responsive to detecting the trigger event, selecting a conditional statement from a set of conditional statements comprising the one or more conditional statements and the plurality of conditional statements; and
presenting, based at least in part on selecting the conditional statement, a fitness communication corresponding to the fitness achievement.

7. The computer-implemented method of claim 6, wherein:
the plurality of conditional statements correspond to at least one preexisting fitness achievement definition; and
the method further comprises:
selecting, in response to detecting the trigger event, a second conditional statement from the set of conditional statements, the second conditional statement corresponding to the at least one preexisting fitness achievement definition; and
presenting, based at least in part on selecting the second conditional statement, a second fitness communication corresponding to the at least one preexisting fitness achievement definition.

8. The computer-implemented method of claim 6, wherein:
the plurality of conditional statements correspond to at least one preexisting fitness achievement definition; and
the method further comprises:
selecting, in response to detecting the trigger event, a second conditional statement from the set of conditional statements, the second conditional statement corresponding to the at least one preexisting fitness achievement definition;
determining that the at least one preexisting fitness achievement definition is no longer capable of being earned by a user; and
removing the at least one preexisting fitness achievement definition from the user device.

9. The computer-implemented method of claim 6, further comprising evaluating, at least in response to selecting the conditional statement, the conditional statement against the at least one fitness achievement criteria using the data tracked by the fitness application to generate an output, and wherein presenting the fitness communication is further based at least in part on the output.

10. The computer-implemented method of claim 9, wherein the output indicates whether the evaluation of the conditional statement is true or whether the evaluation of the conditional statement is false.

11. The computer-implemented method of claim 9, further comprising, in response to evaluating the conditional statement to generate the output, presenting a fitness achievement graphical element in a view of the fitness application on the user device, the view comprising at least one other fitness achievement graphical element corresponding to a preexisting fitness achievement.

12. The computer-implemented method of claim 6, wherein the data tracked by the fitness application comprises at least one of: data identifying a system time change, data identifying an achievement of a fitness goal, data identifying achievement of a particular fitness goal beyond a certain threshold, data identifying completion of a workout, data identifying calories burned, data identifying distance moved, or data identifying a health metric.

13. The computer-implemented method of claim 6, wherein the fitness achievement definition is included in a first asset package, the method further comprising:
   receiving, by the fitness application, a second asset package corresponding to the fitness achievement definition, the second asset package comprising image data corresponding to a fitness achievement graphical element; and
   storing the second asset package on the user device.

14. The computer-implemented method of claim 13, wherein the fitness communication comprises the fitness achievement graphical element and a notification that the fitness achievement has been earned.

15. The computer-implemented method of claim 13, wherein the fitness achievement graphical element is a first fitness achievement graphical element corresponding to an available earned state of the fitness achievement, the image data further comprising a second fitness achievement graphical element corresponding to an earned state of the fitness achievement.

16. The computer-implemented method of claim 6, wherein the fitness communication comprises:
   a notification of a future fitness challenge in which the fitness achievement can be earned; and
   a fitness graphical achievement element that will be awarded if the fitness achievement is earned during the future fitness challenge.

17. The computer-implemented method of claim 6, wherein:
   the user device is a wearable device; and
   the wearable device is configured to use one or more sensors to collect at least a portion of the data tracked by the fitness application.

18. One or more computer-readable storage media storing computer-executable instructions that, when executed by a processor, configure a processor to perform operations comprising:
   managing a plurality of achievement rules stored on a user device;
   receiving data tracked by a fitness application;
   comparing the data to trigger information of a fitness achievement definition to identify a trigger event, the fitness achievement definition comprising:
      an achievement rule having at least one criteria corresponding to a fitness achievement;
      the trigger information identifying the trigger event which occurs independent of fulfillment of the achievement rule; and
      image data corresponding to a fitness achievement graphical element that is specific to the fitness achievement; responsive to identifying the trigger event, responsive to identifying the trigger event, selecting, based at least in part on the fitness achievement definition, at least one achievement rule from a set of achievement rules comprising the plurality of achievement rules and the achievement rule;
   determining that the at least one achievement rule is fulfilled; and
   presenting, at least in response to determining that the at least one achievement rule is fulfilled, a fitness communication corresponding to the fitness achievement and comprising the fitness achievement graphical element.

19. The one or more computer-executable storage media of claim 18, wherein the operations further comprise:
   receiving the fitness achievement definition from a server computer; and
   storing the fitness achievement definition on the user device.

* * * * *